(12) United States Patent
Yacoubian

(10) Patent No.: US 7,463,364 B2
(45) Date of Patent: Dec. 9, 2008

(54) ELECTRO-OPTIC SENSOR

(75) Inventor: Araz Yacoubian, Carlsbad, CA (US)

(73) Assignee: Ler Technologies, Inc., Encinitas, CA (US)

( * ) Notice: Subject to any disclaimer, the term of this patent is extended or adjusted under 35 U.S.C. 154(b) by 0 days.

(21) Appl. No.: 10/902,437

(22) Filed: Jul. 28, 2004

(65) Prior Publication Data

US 2005/0023434 A1    Feb. 3, 2005

Related U.S. Application Data

(60) Provisional application No. 60/579,986, filed on Jun. 14, 2004, provisional application No. 60/491,723, filed on Jul. 31, 2003.

(51) Int. Cl.
G01B 11/02 (2006.01)

(52) U.S. Cl. .................................... 356/502

(58) Field of Classification Search ................ 356/432, 356/502; 73/655, 657
See application file for complete search history.

(56) References Cited

U.S. PATENT DOCUMENTS

| | | | |
|---|---|---|---|
| 5,080,491 A * | 1/1992 | Monchalin et al. | 356/493 |
| 6,543,288 B1 * | 4/2003 | Blouin et al. | 73/643 |
| 6,563,586 B1 | 5/2003 | Stanke et al. | |
| 2004/0125369 A1 | 7/2004 | Wang | |

OTHER PUBLICATIONS

H. T. Grahn, H. J. Maris, and J. Tauc, "Picosecond Ultrasonics," IEEE J. Quant. Elect. 25, 2562-2569 (1989).

H. Maris, "Picosecond Ultrasonics," Scientific American, 86-89 (Jan. 1998).

C. Thomsen, H. T. Grahn, H. J. Maris, and J. Tauc, "Surface Generation and Detection of Phonons by Picosecond Light Pulses," Phys. Rev. B 34, 4129-4138 (1986).

H. T. Grahn, H. J. Maris, J. Tauc, and B. Abeles, "Time-Resolved Study of Vibrations of a-Ge:H/a-Si:H multilayers," Phys. Rev. B 38, 6066-6074 (1988).

C. J. Morath, H. J. Maris, "Phonon Attenuation in Amorphous Solids Studied by Picosecond Ultrasonics," Phys. Rev. B 54, 203-213 (1996).

H.-N. Lin, H. J. Maris, L. B. Freund, K. Y. Lee, H. Luhn, and D. P. Kern, "Study of Vibrational Modes of Gold Nanostructures by Picosecond Ultrasonics," J. Appl. Phys. 73, 37-45 (1993).

H. T. Grahn, D. A. Young, H. J. Maris, J. Tauc, J. M. Hong and T. P. Smith III "Sound Velocity and Index of Refraction of AlAs Measured by Picosecond Ultrasonics," Appl. Phys. Lett 53, 2023-2024 (1988).

H.-N. Lin, R. J. Stoner, and H. J. Maris, "Nondestructive Testing of Microstructures by Picosecond Ultrasonics," J. of Nondestr. Eval. 9, 239-246 (1990).

G. Tas, R. J. Stoner, H. J. Maris, G. W. Rubloff, G. S. Oehrlein, and J. M. Halbout, "Noninvasive Picosecond Ultrasonic Detection of Ultrathin Interfcial Layers: CFx at the Al/Si interface" Appl. Phys. Lett 61, 1787-1789 (1992).

(Continued)

*Primary Examiner*—Tarifur Chowdhury
*Assistant Examiner*—Marissa J. Detschel
(74) *Attorney, Agent, or Firm*—Koestner Bertani LLP; Ken J. Koestner

(57) ABSTRACT

A sensor comprises an optical modulator that generates a modulation signal, an interferometer that mixes an acoustic signal evoked by a pulsed laser with the modulation signal to down-convert the acoustic signal to lower frequencies, and a photodetector that detects the down-converted signal.

47 Claims, 22 Drawing Sheets

OTHER PUBLICATIONS

H.-Y. Hao, H. J. Maris, and D. K. Sadana, "Nondestructive Evaluation of Interfaces in Bonded Silicon-On-Insulator Structures Using the Picosecond Ultrasonics Technique," Electrochemical and Solid-State Lett. 1, 54-55 (1998).

G. L. Eesley, B. M. Clemens, and C. A. Paddock, "Generation and detection of picosecond acoustic pulses in thin metal films" Appl. Phys. Lett 50, 717-719 (1987).

A. C. Diebold, "Metrology technology for the 70-nm node: Process control through amplification and averagin microscopic changes," IEEE Trans. on Semicon. Manufacturing 15, 169-183 (2002).

C. J. Morath, G. J. Collins, R. G. Wolf, and R. J. Stoner, "Ultrasonic Multilayer Metal Film Metrology," Solid State Technology, 85-92 (Jun. 1997).

J. Vollmann*, D. M. Profunser, A. H. Meier, J. Dual, "Ultrasonic wave propagation phenomena at material interfaces of microstructures," SPIE Proc. on Microsystems Engineering, Metrology and Inspection III vol. 5145-24, pp. 180-188, (????).

J. Vollmann*, D. M. Profunser, J. Dual, "High resolution measurement of thin metallic films and multi-layers by femtosecond laser pulses," SPIE Proc. vol. 4400, pp. 82-89, Microsystems Engineering, Metrology and Inspection, Oct. 2001.

J. Vollmann, D. Profunser, J. Dual , "Femtosecond Ultrasonics for the Characterization of Layered Micro- and Nano Structures," Mat. Res. Soc. Symp. vol. 634, pp. B3.3.1-B3.3.5, (2001).

J. Vollmann, D. M.Profunser, J. Dual, "Sensitivity improvement of a pump-probe set-up for thin film and microstructure metrology," Ultrasonics 40, 757-763 (2002).

A. Yacoubian, V. Chuyanov, S. M. Garner, W. H. Steier, A. S. Ren, and L. R. Dalton, "EO Polymer Based Integrated-Optical Acoustic Spectrum Analyzer," J. Selected Topics in Quant. Elect. 6, 810-816 (2000).

A. Yacoubian, "High Frequency Acoustic Spectrum Analyzer Based on Polymer Integrated Optics," Ph. D. dissertation, University of Southern California (1999).

A. Yacoubian, V. Chuyanov, S. M. Garner, H. Zhang, W. H. Steier, A. S. Ren, and L. R. Dalton, "Acoustic Spectrum Analysis Using Polymer Integrated Optics," OSA Proc. on Organic Thin Films for Photonic Applications, 101-103, (Sep. 1999).

A. Yacoubian, "Compact EO polymer vibration sensors utilizing various planar and hybrid fiber/waveguide architectures," Feature Article, Polymer News, 26, 408-415 (2001).

A. Yacoubian, W. Lin, D. Olson, and J. Bechtel, "Compact EO Polymer Vibration Sensor Utilizing Ridge and Slab-Mode Waveguides," ACS Proc. on Polymer Materials: Science and Engineering, 83, 243-244 (Washington DC, Aug. 2000).

J. H. Bechtel, W. Lin, Y. Shi, and A. Yacoubian, "Electro-optic Polymer Integrated Optic Devices for Space Applications," SPIE Proc. Photonics for Space Environments VII, (Jul. 2000).

J. H. Bechtel, and A. Yacoubian, "Recent Advances in Polymer Integrated-Optics Technology," Invited Paper, Proc.. LEOS, (Puerto Rico, Nov. 2000).

F. Tian, R. Ricken, and W. Sohler, "High performance integrated acsouto-optical heterodyne interferometer in LiNbO3," OFS '93, Florence, pp. 263-266, May 4-6, 1993.

F. Tian, R. Ricken, St. Schmid, and W. Sohler, "Integrated acsouto-optical heterodyne interferometers in LiNbO3," LASER '93, Munchen, pp. 725-728, 1993.

D. Jestel, A. Baus, E. Voges, "Integrated-Optic Interferometric Microdisplacement Sensor in Glass With Thermo-Optic Phase Modulation," Electronics Lett., 26, 1144-1145 (1990).

C. Gorecki, "Sub-Micometric Displacement Measurements by an All-fiber Laser Heterodyne Interferometer Using Digital Phase Demodulation," J. Optics 26, 29-34 (1995).

D. Hofstetter, H. P. Zappe, and R. Dandliker, "Monolithically Integrated Optical Displacement Sensor in GaAs/AlGaAs," Electronics Lett. 24, 2121-2122 (1995).

D. Hofstetter, H. P. Zappe, and R. Dandliker, "A Monolithically Integrated Double Michelson Interferometer for Optical Displacement Measurment with Direction Determination," IEEE Phot. Tech. Lett. 8, 1370-1372 (1996).

M. Haruna, T. Yamasaki, H. Hirata, H. Toda, H. Nishihara, "Optical Waveguide Wideband Frequency shifter in Z-Propagating LiNbO3 for Laser Doppler Velocimeter," OFS7, Sydney, Decmeber, pp. 113-116 (1990).

* cited by examiner

US 7,463,364 B2

ELECTRO-OPTIC SENSOR

BACKGROUND OF THE INVENTION

Technical and economic factors continue to drive the evolution of semiconductor processing equipment. The semiconductor industry demands fabrication machines with a capability to process semiconductor wafers at high speed with substantial uniformity and reliability. Integrated circuit fabrication commonly involves numerous process steps with fabrication machinery processing semiconductor wafers at high speed to create structural features with high precision. Measurements are commonly made between process steps to verify features are within tolerances demanding a capability to perform non-destructive inspection and analysis of semiconductor wafers.

Optical metrology is a highly useful technique for non-destructive analysis. Examples of optical metrology include ellipsometry, reflectometry, scatterometry, and others. Ellipsometry involves analysis of changes in polarization state of probe illumination. Reflectometry relates to analysis of changes in illumination intensity. Scatterometry is analysis of diffraction in response to illumination that creates optical scattering of a probe beam. As semiconductor geometries constantly evolve to smaller integrated circuit critical dimensions, optical interrogation wavelengths decrease.

Because the semiconductor fabrication process takes place in a strictly controlled environment, the impact of non-destructive analysis equipment and techniques on the environment is desired to be minimal. Accordingly, desired characteristics of analysis equipment include aspects such as small size, capability to remain conveniently located with respect to process chambers and equipment, capability to perform measurements and analysis without contacting the semiconductor wafers, and capability of remote control.

Measurements are commonly made between process steps. A measurement technique that delays the process awaiting measurement result confirmation between process steps is inherently inefficient. Minimal impact on fabrication throughput is sought. Non-destructive analysis equipment and techniques can improve throughput by reducing or eliminating delay for analysis equipment placement, and reducing time for measurement acquisition and analysis.

SUMMARY OF THE INVENTION

In an illustrative embodiment, a sensor comprises an optical modulator that generates a modulation signal, an interferometer that mixes an acoustic signal evoked by a pulsed laser with the modulation signal to down-convert the acoustic signal to lower frequencies, and a photo detector that detects the down-converted signal.

BRIEF DESCRIPTION OF THE DRAWINGS

Embodiments of the invention relating to both structure and method of operation, may best be understood by referring to the following description and accompanying drawings.

DETAILED DESCRIPTION OF THE EMBODIMENTS

Figure 1:
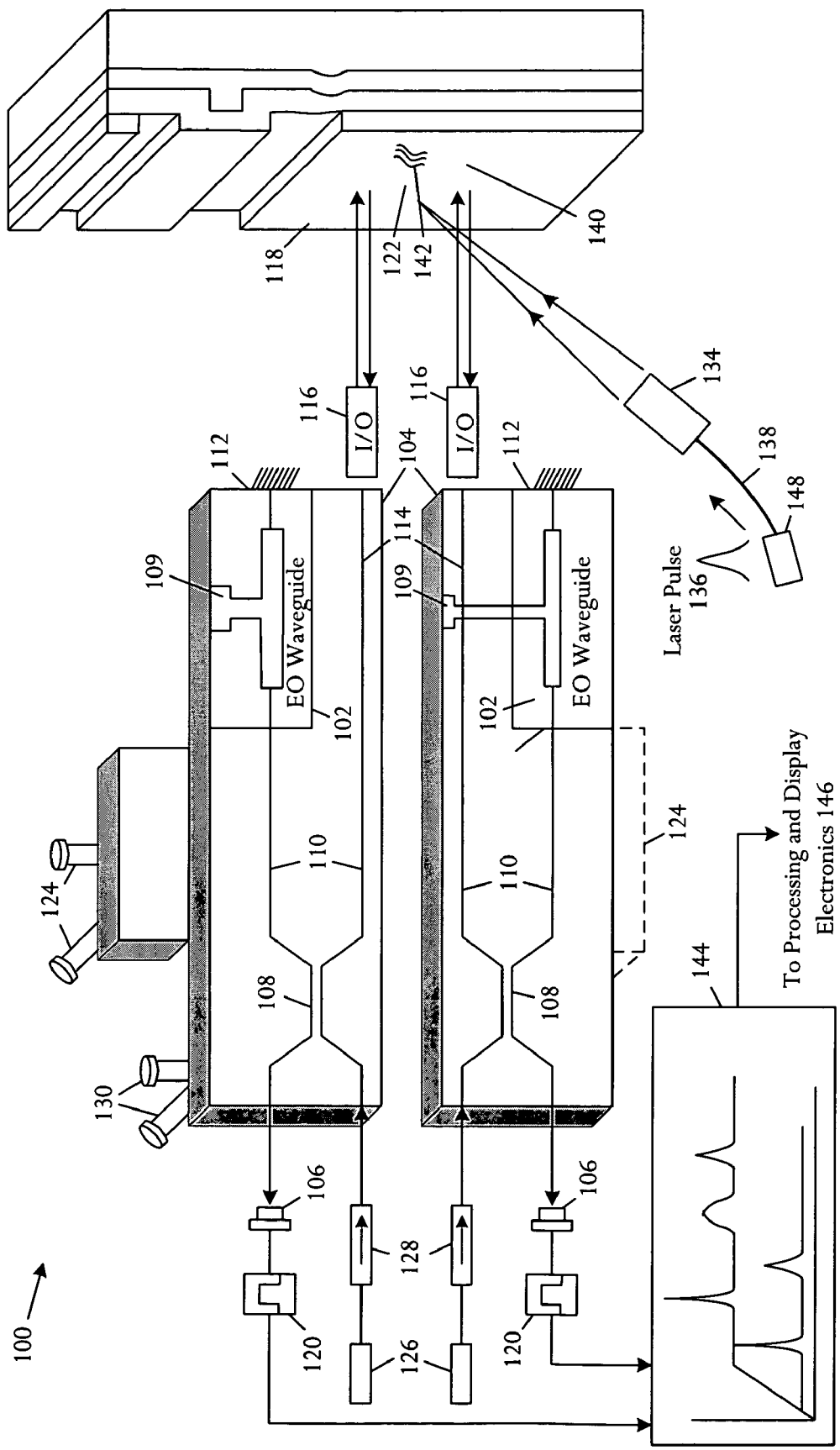
FIG. 1 is a schematic pictorial diagram illustrating an embodiment of an electro-optic sensor.

Sensors in various configurations and arrangements use optical modulators, fiber-optics, and bulk-optic interferometers to perform various measurements. In some applications, the various sensors detect pulsed laser-induced high-frequency acoustic resonance in a multi-layer material. The sensor down-converts high-frequency (GHz) acoustic signals to low-frequency (kHz) detectable signals. The resulting measurement may be either a single point defect signature or a two-dimensional (2D) acoustic "image" indicating subsurface defects. Defect examples include delamination, thickness variation, cracks, inclusions, and damaged micro- or nano-structure. Various architectures may be used for single point measurements and two-dimensional (2D) measurements, acquired in normal incidence and arbitrary angle of incidence measurements. The appended drawings depict several examples of suitable sensor structures.

The illustrative sensors and devices can be used for a variety of detection schemes. Examples of some of detection schemes are presented. Any of the depicted sensors can be used with any of the disclosed schemes, enabling a wide range of detection capability.

In some embodiments, a sensor architecture uses two parallel Michelson interferometers.

Some embodiments disclose sensor architectures that use a cascaded amplitude modulator/interferometer architecture.

One aspect of some of the embodiments shown herein is a cascaded interferometer architecture for acoustic signal detection and down-conversion.

In some configurations, sensors may include a light modulator and an interferometer that mixes the modulation signal with a pulsed laser induced acoustic signal to down-convert the signal to low frequencies for detection using a photo-detector.

The various sensors may be configured to detect subsurface structure by monitoring a pulsed laser induced change in the refractive index near the surface of the sample under test.

In some of the illustrative techniques, a surface vibration detection method enables detection of delamination.

In other techniques described herein, a surface vibration detection method detects excess materials in micro-electromechanical systems (MEMS) and to detect defects in a single layer and multiple layers.

In other illustrative techniques, a method detects pulsed laser induced near surface refractive index change to image subsurface structures.

The optical sensor technology in various configurations can detect defects in semiconductor integrated circuits (IC) in real time, as defects occur during IC fabrication. The integrated electro-optical sensors can be constructed of optical waveguides and specialty optical polymers and configured in a compact sensor head which is capable of resolving fine defects, for example in the sub-micron, nanometer length scale. The technology can be implemented with one or more of various beneficial aspects including a non-contact arrangement, capability for non-destructive testing, high-resolution performance, and a suitability for industrial applications since mechanical isolation is unnecessary since completely electrical control is possible. Furthermore, the technology can be highly compact by virtue of a basis on waveguide design.

Referring to FIG. 1, a schematic pictorial diagram illustrates an embodiment of a sensor 100 comprising an optical modulator 102, an interferometer 104, and a photo-detector 106. The optical modulator 102 generates a modulation signal. The interferometer 104 mixes an acoustic signal evoked by a pulsed laser with the modulation signal to down-convert the acoustic signal to lower frequencies. The photo-detector 106 detects the down-converted signal.

In the illustrative embodiment, two active interferometers 104 are arranged at relatively close proximity to one another. For example, each interferometer may be a Michelson interferometer biased at zero phase difference between the two interferometer arms. Beam splitting can be attained by using a 50:50 directional coupler 108. The interferometers may be constructed as integrated circuit waveguide devices, arranged in a configuration of multiple layers, described from bottom to top. A bottom substrate layer, for example constructed from glass or silicon (Si) can be overlaid by a metallic ground plane, a lower cladding, a core layer, an upper cladding, and a radio-frequency (RF) electrode 109, typically a metal layer.

Waveguide layers such as the cladding and core layers can be either polymeric, crystalline, or semiconductor layers. The core has higher refractive index than the upper and lower cladding layers to confine light in the out-of-plane direction. In-plane light confinement is achieved using ridge or channel waveguides 110, shown as lines in FIG. 1, which are etched either in the core or in one of the cladding layers.

The waveguides 110, for example either the entire core layer or part of the core layer is an active element. Typically, the active element is electro-optically active, electro-absorptive, and the like. A reflective coated endface 112 of the waveguide 110 functions as a reference mirror. A second waveguide end 114 is out coupled via an input/output device 116, for example gradient index lens or a fiber collimator. Light is reflected back from the surface or near the surface of a sample under test 118. Reference and signal beams are combined at the photo-detector 106. At the zero bias point, the interferometer 104 has a quadratic response, and the phase modulation on the light caused by the vibrating surface (or due to elastic wave induced change in the refractive index near the surface) mixes with the phase modulation due to the electro-optic (EO) element 102. The acoustic signal (GHz) is down converted to lower frequencies (kHz-MHz) and is detected by a lower-frequency photo-detector 106. Immediately after the detector 106, a low pass (homodyne) or a band-pass (heterodyne) filter 120 is used to filter unwanted frequencies. When a beat frequency falls within the filter's bandwidth, a high amplitude signal is obtained. When the beat frequency is out of the filter's range, a low amplitude signal is obtained.

FIG. 1 depicts a simplified schematic showing the sensor 100, which functions as an integrated optical acoustic spectrum analyzer. Two active, for example electro-optical (EO) Michelson interferometers 104 are used at close proximity, for example typically within a few centimeters or millimeters, for a better quantification of the damage, enabling estimation of size of damaged area 122. Distance between the two interferometers is variable and adjustable using interferometer separation adjustment controls 130. The electro-optical Michelson interferometers 104 receive laser illumination from lasers 126 via isolators 128. The electro-optic phase modulator 102 is coupled to the waveguide 110. The input/output optics 116 can be a gradient index lens, either fiber coupled or lens coupled. The illustrative embodiment includes a band-pass filter (BPF) 120 that filters the signal received at the photo-detector (PD) 106. The sensor head 100 may be mounted on an optional x-y scanner 124 for acquisition of a two-dimensional defect acoustic spectrum.

The sample 118 is interrogated using an interrogation pulsed laser 148 that delivers a laser pulse 136 via an optical fiber 138 focused with a lens 134. In the illustrative example, the defective area 122 can be distinguished from a defect-free area 140 by analysis of elastic waves 142 generated from the sample using data acquisition electronics 144 which receives signals from the interferometers 104 and communicates the signals to processing and display electronics 146.

The geometry of two Michelson interferometric sensors 104 arranged at close proximity serves two purposes. First, the arrangement generates additional information for determining severity of the damage/defect by comparing the spectra of the two adjacent sensors. Second, the defect size can be determined by varying the distance between the two Michelson interferometers 104 while observing the difference in spectra, enabling measurement of average defect size, another measure of severity of the damage/defect.

Figure 2:
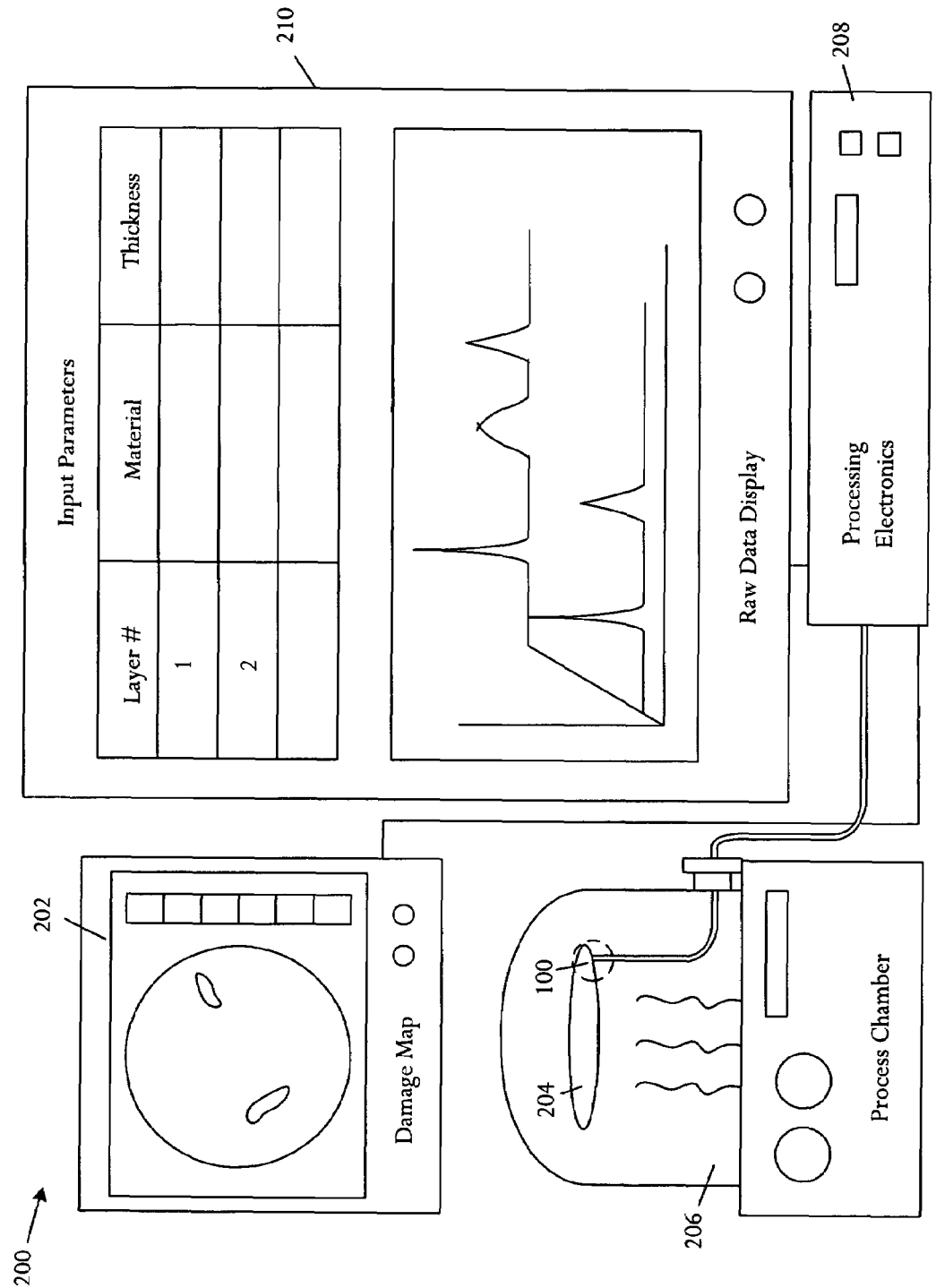
FIG. 2 is a schematic pictorial and block diagram illustrating an embodiment of a test configuration using the electro-optic sensor.

Referring to FIG. 2, a schematic pictorial and block diagram illustrates an embodiment of a test configuration 200 using the electro-optic sensor 100. The example illustrates use of the sensor 100 to perform real time, in-situ defect detection during semiconductor processing. A single point or small area interrogation can be performed in real time. A complete wafer scan can be performed between semiconductor processing steps, enabling viewing of a two-dimensional defect/damage map 202. A semiconductor wafer 204 is tested using the electro-optic sensor 100 in a process chamber 206. Signals from the sensor 100 are transferred to processing electronics 208 for analysis and display on a raw data display 210.

Referring again to FIG. 1, light intensity at the photo-detector (PD) 106 can be modeled according to equation (1) as follows:

$$I(t) = r(1-r)I_o\{2 + 2\cos[\phi_s \cos(\omega_s t) - \omega_m \cos(\omega_m t) + \phi_d]\} \quad (1)$$

where r is the optical waveguide coupling coefficient (for example 0.5 for 50:50 coupler), $I_o$ is the input light intensity, $\phi_s = (2\pi/\lambda)\Delta_s$ where $\Delta_s$ is the acoustic signal amplitude, $\lambda$ is the light wavelength, and $\phi_m = (2\pi/\lambda)\Delta n_{EO} L$, where L is the active (for example, electro-optical) element length. If the entire core is active or composed of electro-optical material, then L is the length of the RF electrode 109 shown in FIG. 1. Index variation ($\Delta n_{EO}$) is the index variation due to electro-optic modulation and $\phi_d$ is the phase difference between the two arms of the interferometer 104. Angular frequencies $\omega_s$ and $\omega_m$ of the vibration and the electro-optical modulation are respectively $\omega_{s,m} = 2\pi f_{s,m}$. By setting the interferometer 104 to zero bias, for example $\phi_d = 0$, and for small amplitude vibrations, equation (2) results as follows:

$$I(t) = r(1-r)I_0\left\{4 - \frac{\phi_s^2}{2}[1-\cos(2\omega_s t)] - \frac{\phi_m^2}{2}[1-\cos(2\omega_m t)] + \phi_s \phi_m \cos[(\omega_s - \omega_m)t] + \phi_s \phi_m \cos[(\omega_s + \omega_m)t]\right\} \quad (2)$$

The difference frequency term, $\omega_s - \omega_m$, in equation (2) denotes frequency down conversion. A low-pass or band-pass filter 120 eliminates higher order terms.

The illustrative sensor 100 and associated technique are capable of detecting phenomena including surface vibration or changes in refractive index. Surface vibration detection is useful for a single layer system. Detection of changes in refractive index near the surface of the sample is useful for interrogating multi-layer systems. For a cantilever-type or free standing structures, for example micro-electromechanical systems (MEMS) or delaminated films, surface vibrations occur. In a multi-layer system, the acoustic pulse wave reflects from various layer interfaces and travels back to near the sample surface. Strain induced by the acoustic pulse wave changes the optical properties near the surface, and both the refractive index ($\Delta n_s$) and absorption ($\Delta\alpha$) are modulated. The modulated signal carries information about the multi-layer system including layer density, acoustic velocity, thickness, and others, as well as presence of defects such as improper adhesion gaps and the like. When light from the sensor 100 enters the sample 118, the reflected wave near the surface 142, for example from the first and second layer interface, is modulated due to the modulated refractive index $\Delta n_s$. If the entire structure is also vibrating or if surface waves are present, the modulated signal has a much lower frequency than the frequency of modulation of $\Delta n_s$ due to multi-layer structure. Therefore a high-frequency spectrum yields information about the subsurface thin film structure. The illustrative sensor 100 and technique are useful even with "opaque" films, such as metals and semiconductors, since some light penetration of the film always occurs. Furthermore, various wavelengths can be used to optimize depth penetration for a specific multi-layer system. Light reflected from the non-modulated does not generate an error signal since heterodyning filters the direct current (DC) part of the spectrum. Multiple various detection methods are described herein.

Figure 3:
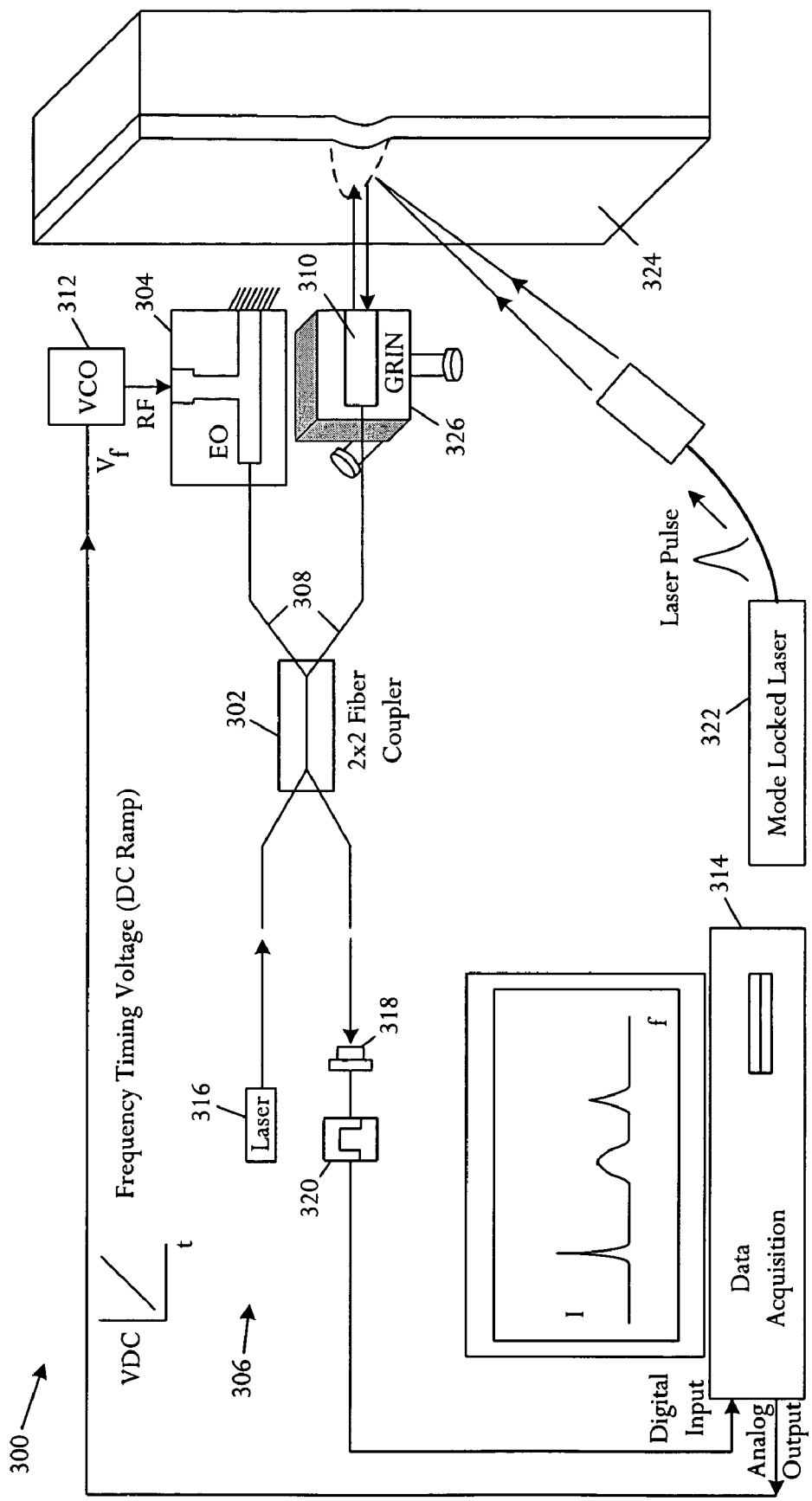
FIG. 3 is a schematic pictorial and block diagram depicting an embodiment of a sensor that is configured using fiber couplers and phase modulators.

Referring to FIG. 3, a schematic pictorial and block diagram illustrates an embodiment of a sensor 300 that is configured using fiber couplers 302 and phase modulators 304. Although FIG. 3 shows only one Michelson interferometer 306, a two-interferometer configuration can be constructed by combining two of the interferometers 306 in parallel. The all-fiber sensor 300 as an alternative to an integrated optical sensor 100 shown in FIG. 1 also has polarization controllers that are not illustrated, but may be located in the interferometer arms 308 and at the input interface to the interferometer 306 to improve sensor performance. An illustrative sensor 300 may include an electro-optic (EO) phase modulator 304 or other type of modulator. A voltage controlled oscillator (VCO) 312 receives a frequency tuning voltage, for example a DC ramp, from data acquisition electronics 314 and generates a radio frequency (RF) signal that is applied to the modulator 304. A laser 316 supplies illumination to the Michelson interferometer 306. A photo-detector 318 receives a modulated signal from the interferometer 306 that can be filtered, for example using a bandpass filter 320. An interrogating laser 322, for example a mode-locked laser, generates a laser pulse that is applied to a sample under test 324. The illustrative Michelson interferometer 306 uses gradient index lenses (GRIN) 310 to send and receive illumination from the sample 324. An x-y scanner 326 may be used to acquire spatial information.

One consequence of all-fiber sensor usage is high sensitivity to environmental changes. In contrast, the integrated sensor 100 shown in FIG. 1 typically has better vibration stability since the two arms of each Michelson interferometer 104 are at close proximity, for example within tens of microns, so that any thermal or mechanical variations affect both arms of the interferometer 104 equally, canceling or minimizing the effect.

Figure 4:
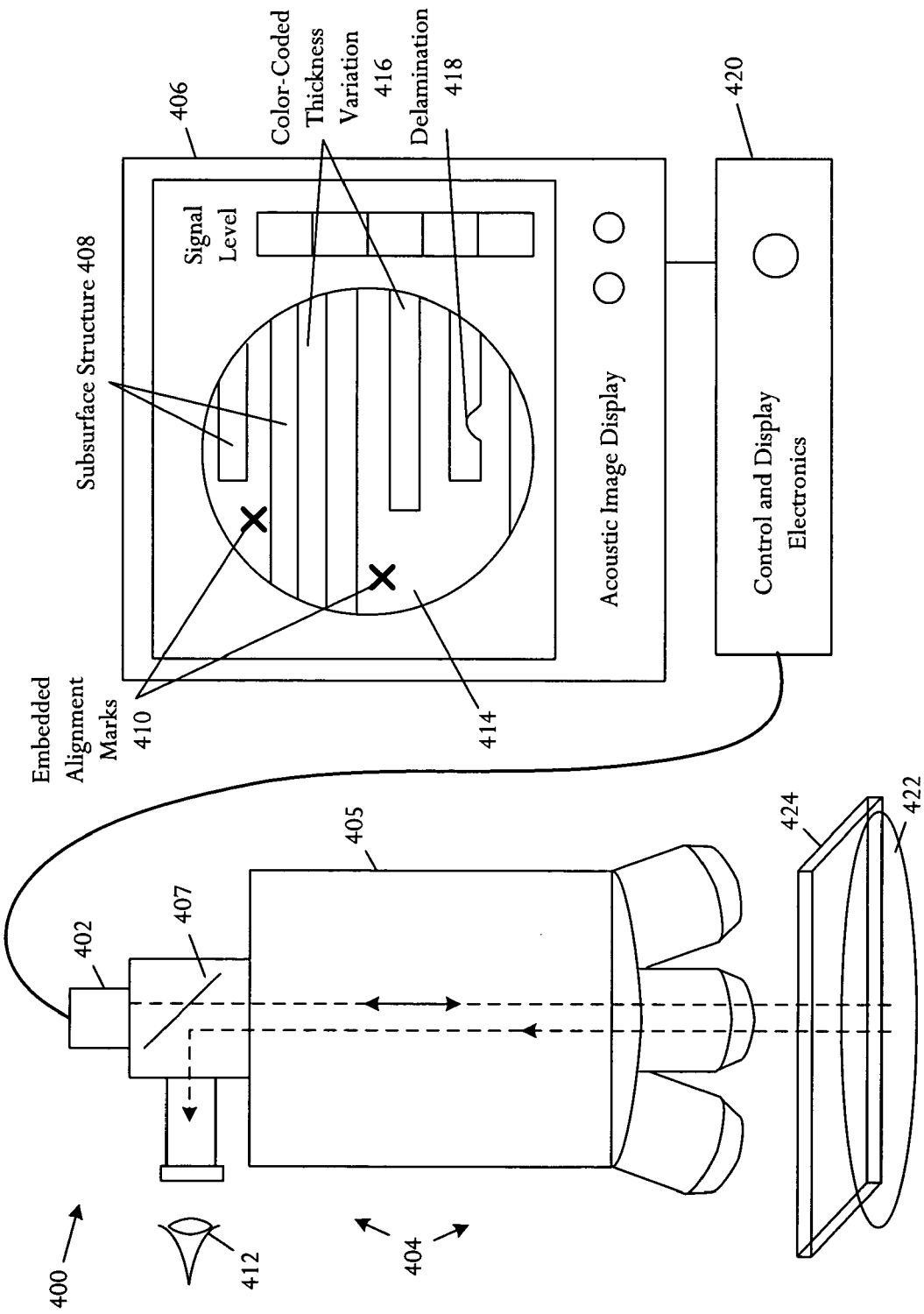
FIG. 4 is a pictorial and block diagrams showing an embodiment of a test configuration that can use an alternative electro-optic sensor.
Figure 5:
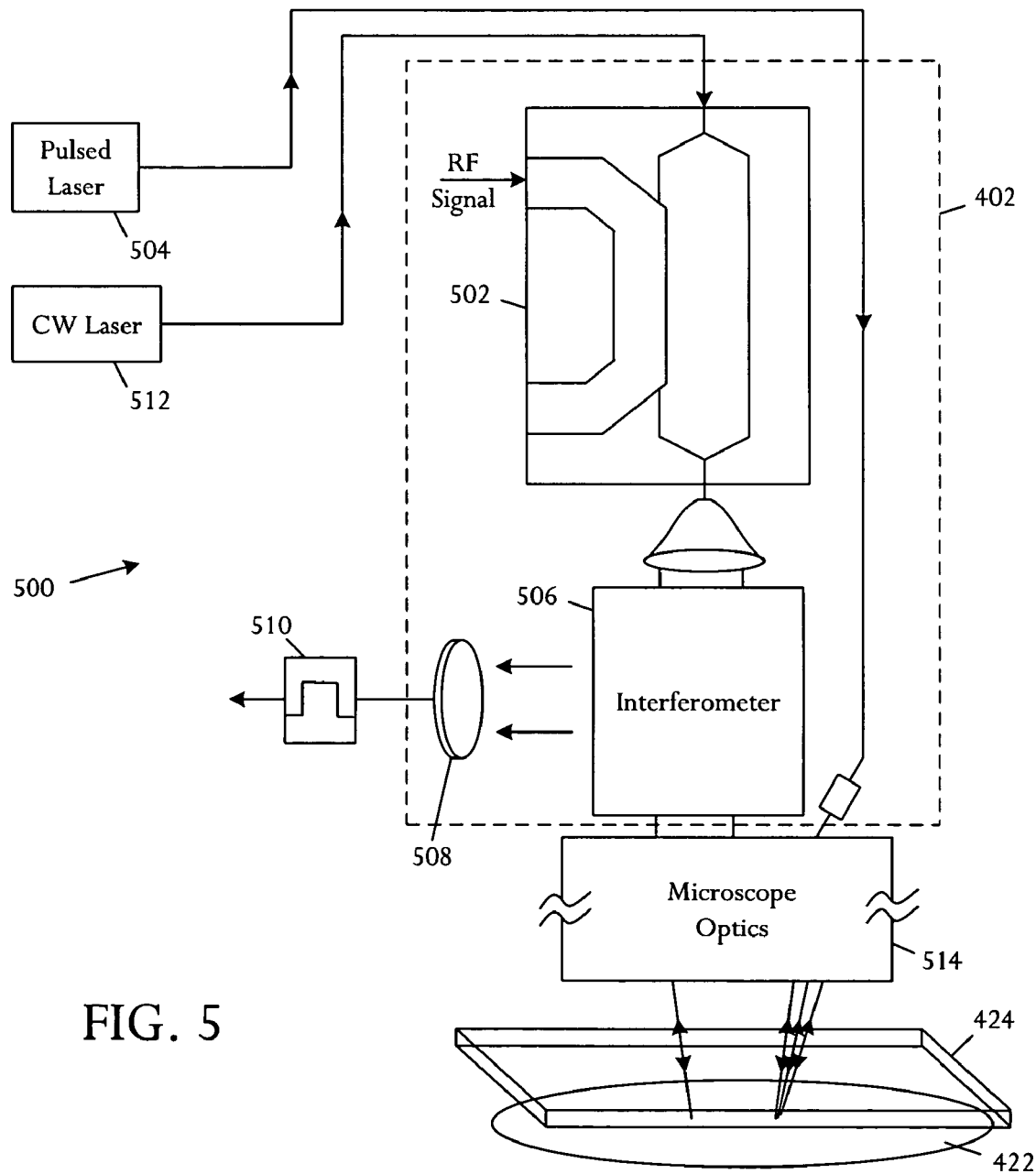
FIG. 5 is a schematic pictorial and block diagram illustrating and an embodiment of an alternative electro-optic sensor used in the test configuration shown in FIG. 4.

Referring to FIGS. 4 and 5, combination pictorial and block diagrams show an embodiment of a test configuration 400 and an embodiment of an alternative electro-optic sensor 500 that can be used in the test configuration 400. In the test configuration 400 depicted in FIG. 4, a sensor 402 is mounted on a mask aligner 404 that includes a microscope 405 and internal beam splitter 407. A high-frequency, narrowband acoustic signal amplitude display 406 reveals subsurface structure 408 and embedded alignment marks 410 that may not be visible to the eye or a CCD camera 412. An acoustic image 414 can also indicate defects, such as thickness variation 416 and delamination 418. For example, a color-coded image can be used to indicate layer thickness variation 416.

In one operative example, the test configuration 400 uses the sensor 402 to interrogate subsurface structure of a wafer 422 through a lithographic mask 424 during lithography. The sensor 402 is used as an attachment to a mask aligner 404. In the illustrative sensor application, the sensor 402 may perform other operations in addition to mask alignment. Control and display electronics 420 can be manipulated to perform various tests and measurements.

Referring to FIG. 5 in combination with FIG. 4, the sensor 402 uses a modulator 502, illustratively shown as an electro-optic (EO) Mach-Zehnder modulator, to perform subsurface interrogation by exciting high-frequency acoustic waves using a pulsed laser 504 and detecting the waves using a cascaded active 502/passive interferometer 506. The sensor 402 down-converts a high-frequency, for example gigahertz (GHz) range, acoustic signal to a low-frequency detectable signal. The detectable signal is typically in a range from kilohertz (kHz) to megahertz (MHz) and is detected by heterodyning—mixing the optical phase induced by the acoustic and RF signals. The result is a two-dimensional image of the subsurface structure.

The sensor 402 also includes a photo-detector (PD) 508 and a Band Pass Filter (BPF) 510 that pass modulated and heterodyned signals out to control and display electronics 420. Interferometer 506 can be a bulk-optic Michelson interferometer, such as the interferometer shown in FIG. 6.

The sensor 402 depicted in FIG. 5 may include two cascaded interferometers 502 and 506, one an active integrated optical interferometer such as an electro-optic (EO) Mach-Zehnder modulator 502. The second interferometer can be a bulk optic Michelson interferometer 506. In the cascaded arrangement, phase modulation on the light resulting from surface vibration or from elastic wave-induced change in the refractive index near the sample surface, mixes with the phase modulation resulting from operation of the electro-optic (EO) element 502. A continuous wave (CW) laser signal from a CW laser 512 is applied to the electro-optic modulator 502 to activate modulation. A radio frequency (RF) signal is applied to the electro-optical modulator 502, thereby applying a tuning frequency. The sensor 402 interrogates the test wafer 422 by illumination through microscopic optics 514.

Figure 6:
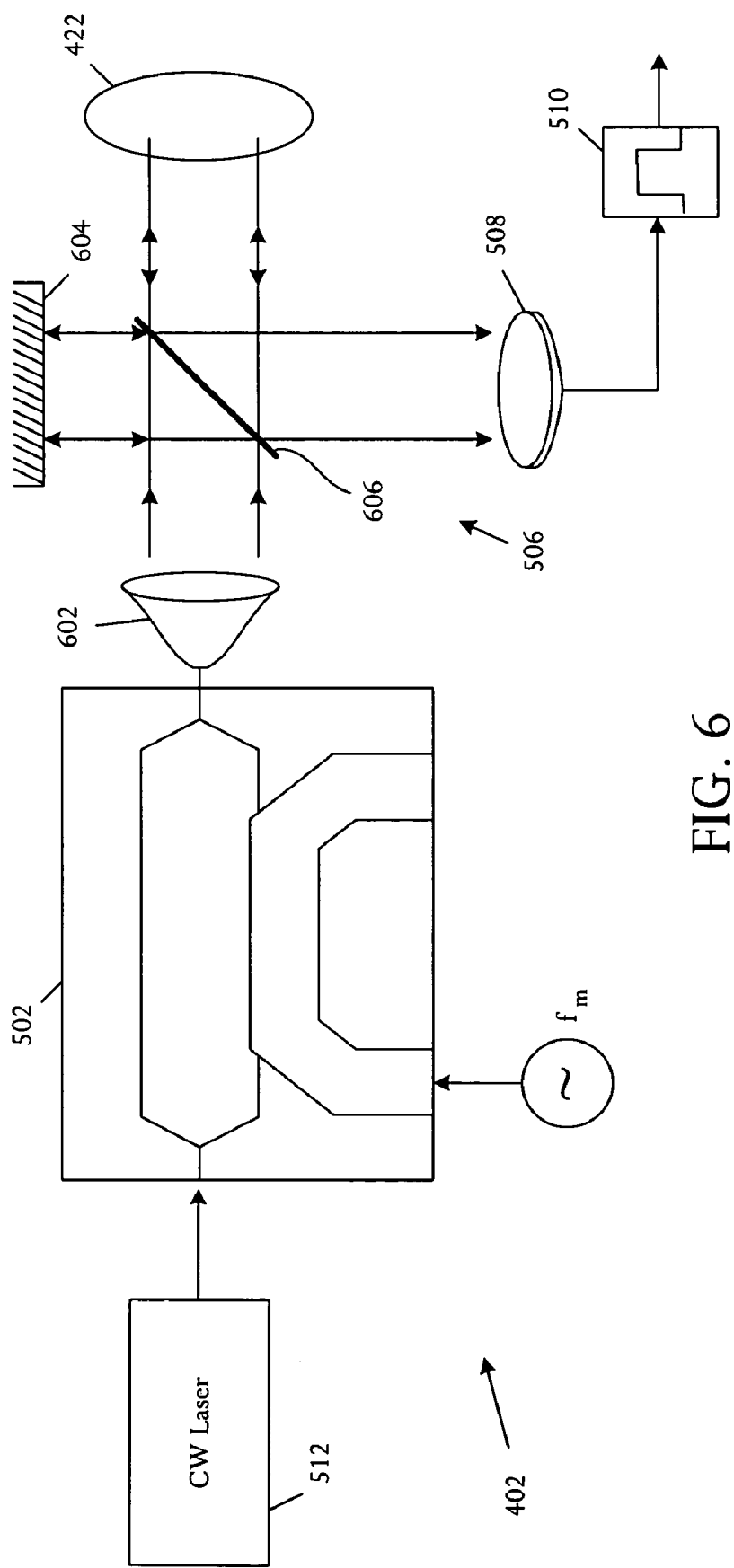
FIG. 6 is a schematic pictorial and block diagram depicting an embodiment of the sensor also shown in FIGS. 4 and 5 and illustrating additional detail.

Referring to FIG. 6, a schematic pictorial and block diagram illustrates an embodiment of the sensor 402 also shown in FIGS. 4 and 5 with additional detail. The sensor 402 includes the Michelson interferometer 506, an electro-optic (EO) Mach-Zehnder modulator 502, an electrical band-pass filter (BPF) 510, and a two-dimensional photo-detector (2 DPD) 508. A reference mirror 604 and a beam splitter 606 are shown in the Michelson interferometer 506. Optical signals are coupled from the Mach-Zehnder modulator 502 to the Michelson interferometer 506 via a collimating lens 602. The signal frequency $f_m$ applied to electro-optic modulator 502 is alternatively references as a radio frequency (RF) signal.

When the cascaded interferometers 502, 506 are biased at quadrature, light intensity at the photo-detector (PD) 508 can be modeled according to equation (3) as follows:

$$I(t) = \frac{I_0 T}{4} \{1 - \sin[X_m \sin(\omega_m t + \phi_m)]\} \cdot \{1 - \sin[X_a \sin(\omega_a t + \phi_a)]\} \quad (3)$$

where, $I_o$ is the input light intensity, T is the coupling and the transmission loss through the interferometers 502, 506 when the interferometers are biased at maximum transmission. Parameters X, ω and φ refer to signal amplitude, angular frequency and phase. Subscripts m and a identify electro-optic modulation and acoustic signal, respectively. For equation $X_m = \pi V_m / V_\pi(\omega_m)$, $V_m$ is the RF signal amplitude and $V_\pi(\omega_m)$ is the RF half-wave voltage of the modulator 502 at angular frequency $\omega_m$. In equation $X_a = (2\pi/\lambda)\Delta_a$, parameter $\Delta_a$ is the acoustic signal amplitude and λ is the light wavelength. Expanding equation (3) using Bessel functions (J), and ignoring the higher order terms yields equation (4) as follows:

$$I(t) = \frac{I_0 T}{4} \cdot \{1 - 2J_1(X_m)\sin(\omega_m t + \phi_m) - 2J_1(X_a)\sin(\omega_a t + \phi_a)$$

$$-2J_1(X_m)J_1(X_a)[\sin[(\omega_m - \omega_a)t + \phi_m - \phi_a] + \sin[(\omega_m + \omega_a)t \phi_m + \phi_a]]\} \quad (4)$$

The difference frequency ($\omega_m - \omega_a$) term in equation (4) denotes frequency down-conversion. A low-pass or band-pass filter 510 eliminates higher order terms. When the interferometers 502, 506 are not biased at quadrature, higher-order terms are present, such as $2\omega_m - \omega_a$ and $2\omega_a - \omega_m$. Therefore active biasing of the interferometers 502, 506 can produce a better measurement signal.

Figure 7:
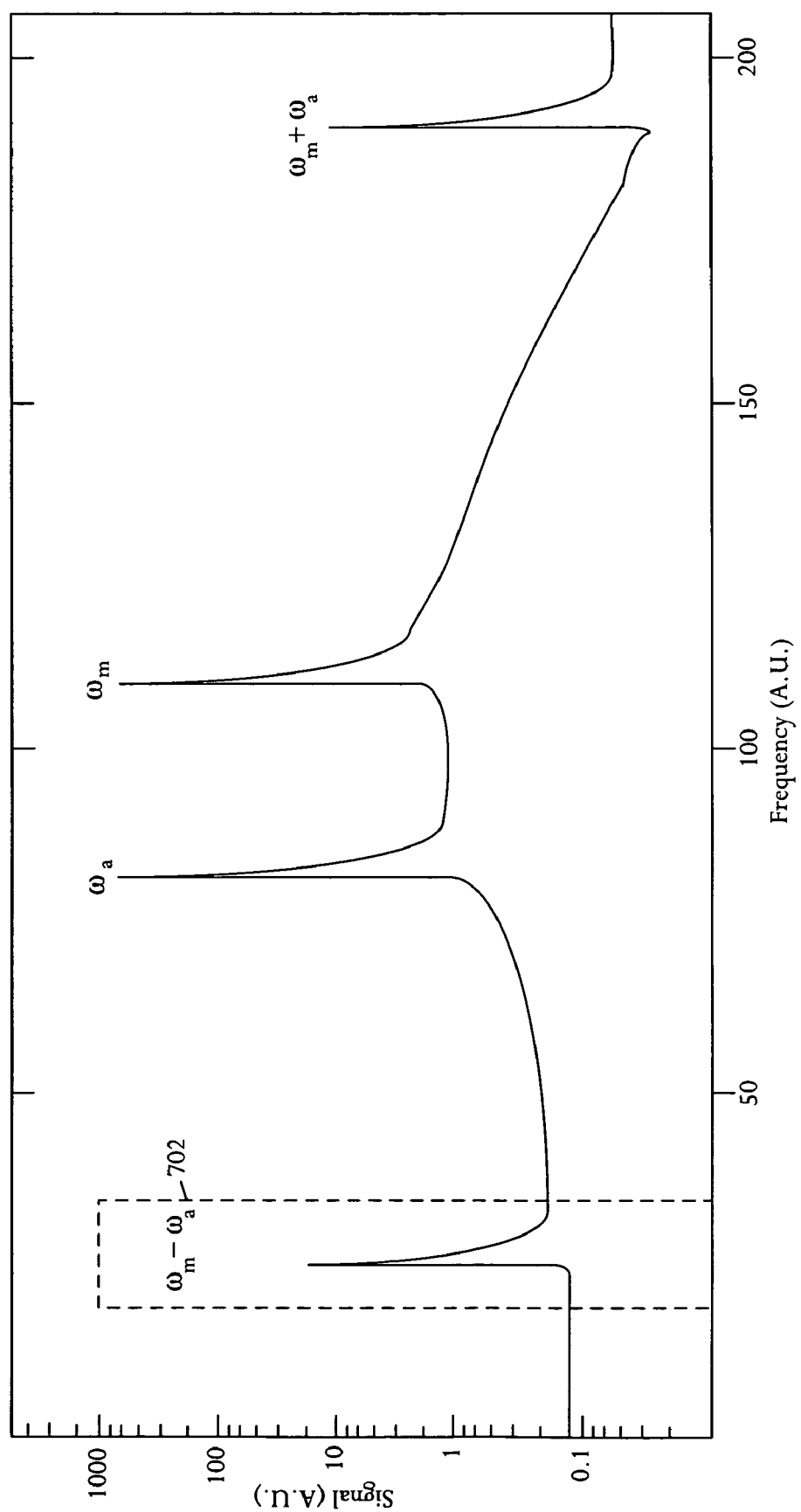
FIG. 7 is a frequency response graph illustrating mixing of the electro-optic and acoustic signals.

Referring to FIG. 7, a frequency response graph shows results of a simulation of equation (3) so illustrate mixing of the electro-optic and acoustic signals. The frequency response is computed by taking the Fast Fourier Transform of current I(t). Simulation of the sensor 402 shown in FIGS. 4, 5, and 6 produces a response using equation (3) with $X_m = X_a = 0.1$, $\phi_m = \phi_a = 0$, and $I_o T/4$ is set to unity. Dashed line 702 indicates operation of the band-pass filter 510 that passes only the difference frequencies.

The equation term $\omega_m - \omega_a$ specifies the difference frequencies. Higher order terms are filtered by a low-pass or a band-pass filter 510 placed after the photo-detector 508. The filter 510 is generally designed to pass only the difference frequency as illustrated with a dashed line 702. Therefore the acoustic signal, for example in a high-frequency such as gigahertz (GHz) range, is down-converted to lower frequencies, for example in a kilohertz to Megahertz range (kHz-MHz), and is detected by the lower-frequency photo-detector 508. Immediately after the detector 508, a low pass (homodyne) or a band-pass (heterodyne) filter 510 is used to filter out the unwanted frequencies. When the beat frequency falls within the filter's bandwidth, a high amplitude signal is obtained. When the beat frequency is out of the filter's range, a low amplitude signal is obtained. Thus, variations in the acoustic resonance frequencies are detected.

In equation (4), terms $J_1(X_m)J_1(X_a) \sim X_m X_a / 4$ for $X_{m,a} \ll 1$. Therefore, to detect low amplitude acoustic signals, the RF drive voltage can be increased.

In the sensor 402 depicted in FIGS. 5 and 6, light from the Mach-Zehnder electro-optic modulator 502 is expanded and collimated. Reflected light from the sample surface or from near the surface interferes with the reference beam of the interferometer 506 at the two-dimensional photo-detector 508.

Figure 8A:
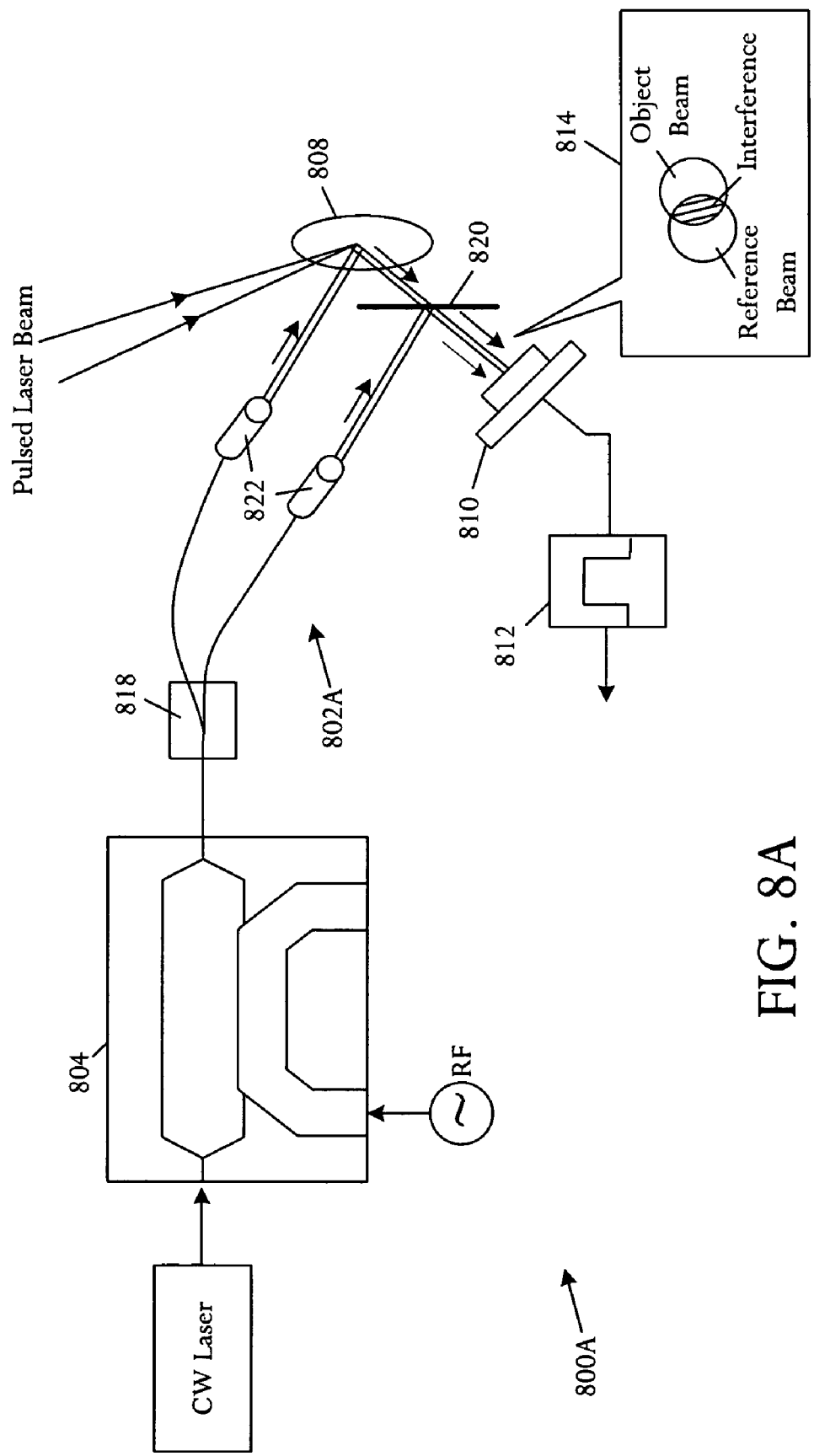
FIGS. 8A, 8B, and 8C are mixed pictorial and block diagrams showing variations of an embodiment of a third sensor architecture.
Figure 8B:
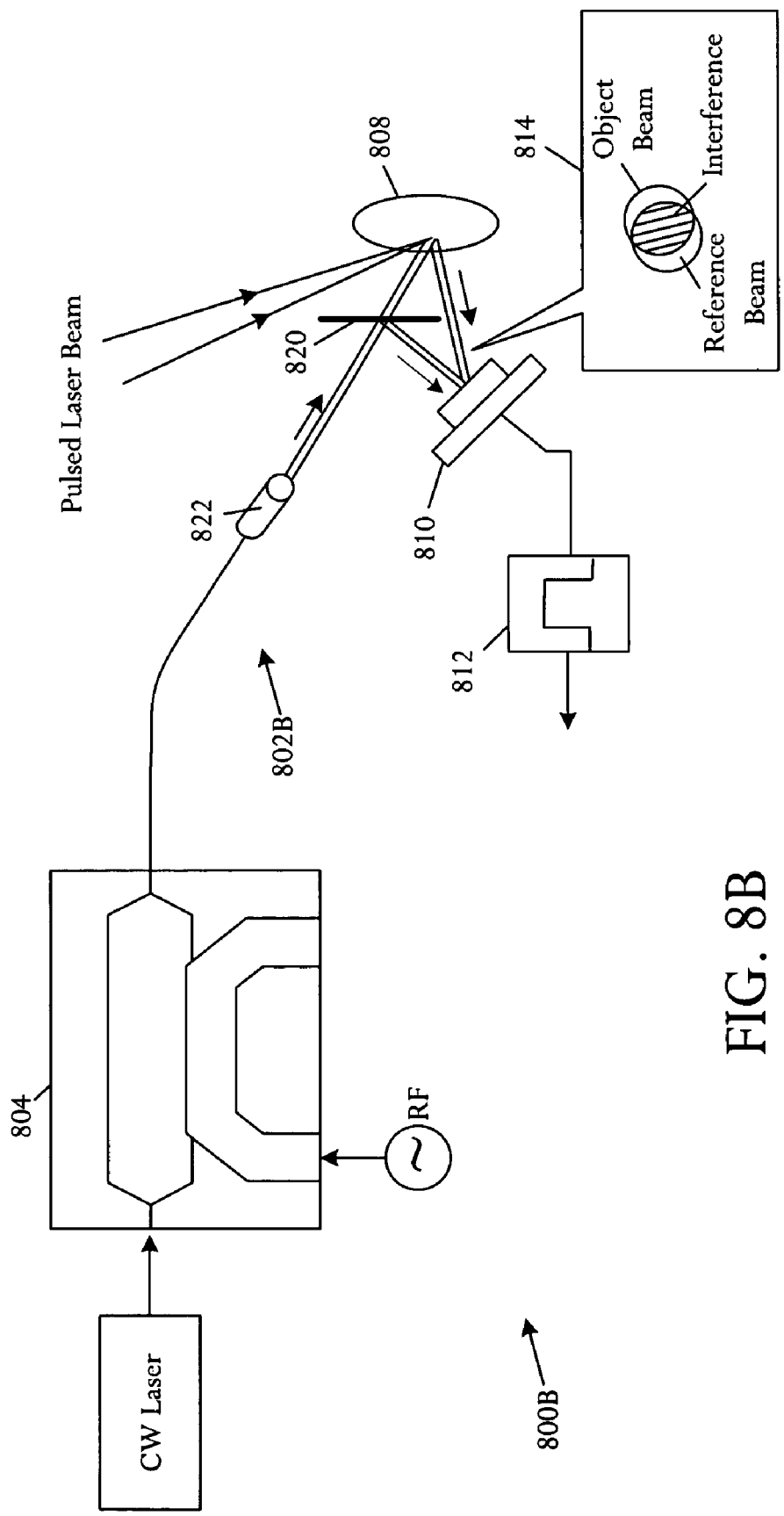
Figure 8C:
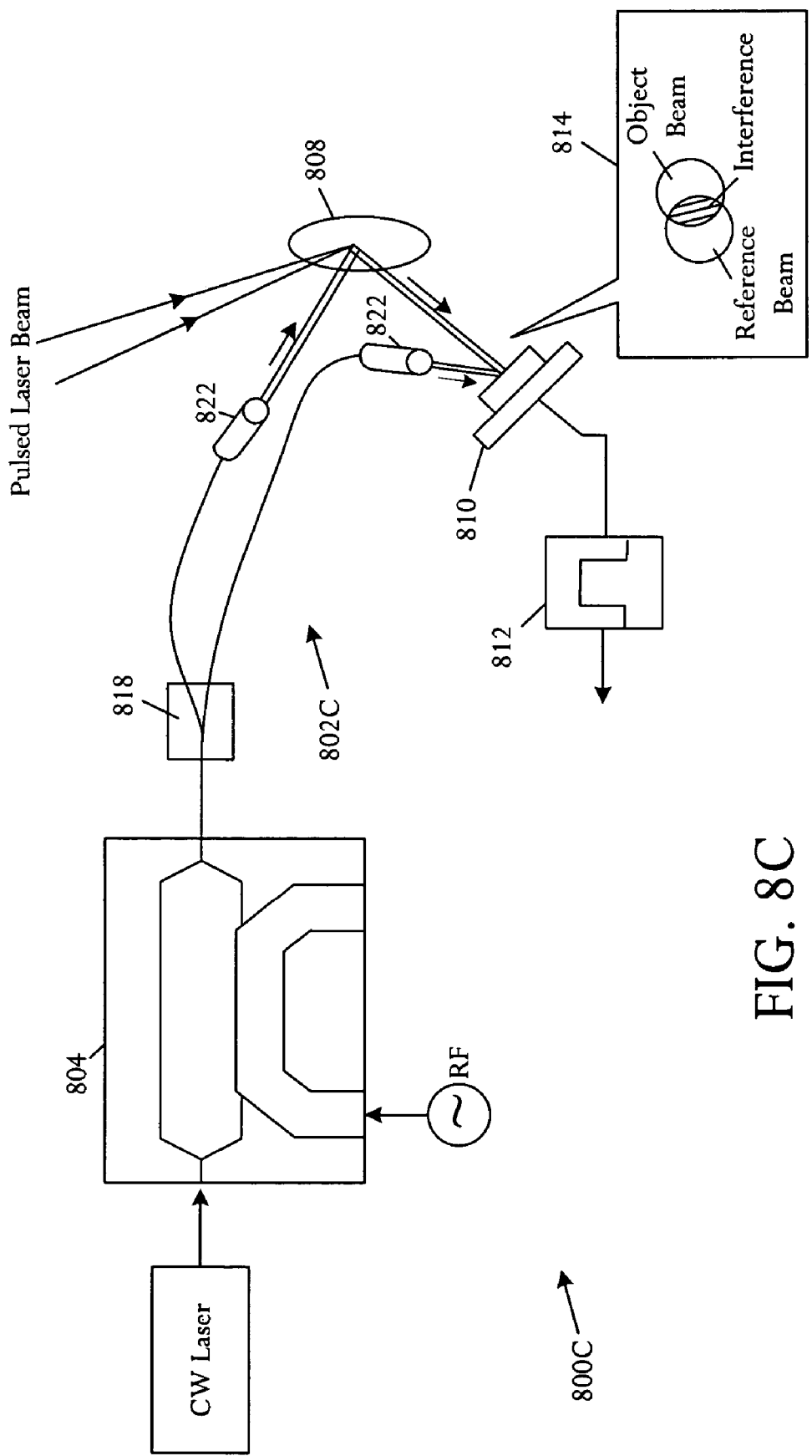

Referring to FIGS. 8A, 8B, and 8C, mixed pictorial and block diagrams illustrate embodiments of a third sensor architecture. The third architecture sensor 800A-C is similar to the cascaded Mach-Zehnder/Michelson structure 402 depicted in FIGS. 4, 5, and 6, except the output device is not a Michelson interferometer. Instead, the sensor 800A-C uses a two-beam interference 802A-C instead of a Michelson interferometer at the output terminal of a Mach-Zehnder modulator 804. The interference 802A-C is attained by interfering two beams. One is a signal beam, which is light reflected from the sample surface or near surface, and another is a reference beam. Three example embodiments of device schematics are shown in FIGS. 8A, 8B, and 8C. Collimating lenses shown in FIGS. 8A, 8B, and 8C can be either gradient index lenses (GRIN), or other collimating lenses.

In the illustrative embodiments, light is modulated using a Mach-Zehnder modulator 804 although in other configurations and arrangements other types of modulators may be used. The optical output signal from the modulator 804 is split into two using the various configurations shown in FIGS. 8A, 8B, and 8C. One part of the light, called the signal beam, is reflected from the sample. A second part of the light is received as a reference beam. The two beams are combined at a photo-detector (PD) 810 and are interfered as shown in the inset 814. A filter, such as a band-pass filter (BPF) 812 filters out high frequencies. Sensor 800A-C down-converts a high-frequency acoustic signal to a low-frequency detectable signal.

Any of the three configurations shown in FIGS. 8A, 8B, and 8C can be used either for a single point detection using a one-dimensional photo-detector 810, or for a two-dimensional interrogation using a two-dimensional detector 810. For a single point photo-detector, either the detector aperture should be smaller than the fringe spacing, or a pinhole or an iris should be used in front of the photo-detector which is smaller than the fringe separation. If a two-dimensional photo-detector is used, the fringe spacing is to be larger than the pixel size to improve or optimize fringe movement detection.

Sensor 800A shown in FIG. 8A uses a 1×2 fiber coupler 818 to split light at the output of the modulator 804, direct the two beams through collimating lenses 822, and recombine the light by using a beam splitter 820.

Sensor 800B shown in FIG. 8B uses a single fiber output and splits the single beam using a beam splitter 820, sending one part of the light to the sample 808 which is then reflected to the detector 810 as the signal beam. The other part of the light goes to the detector 810 as the reference beam.

Sensor 800C depicted in FIG. 8C is similar to sensor 800A but may omit usage of an additional beam splitter. Instead one fiber collimator 822 is directed to the sample 808 and a second fiber collimating lens 822 is directed to the detector 810. Reflected light from the sample 808 as the signal beam interferes with the collimated light from the other lens 822 as the reference beam at the photo-detector 810.

Figure 9:
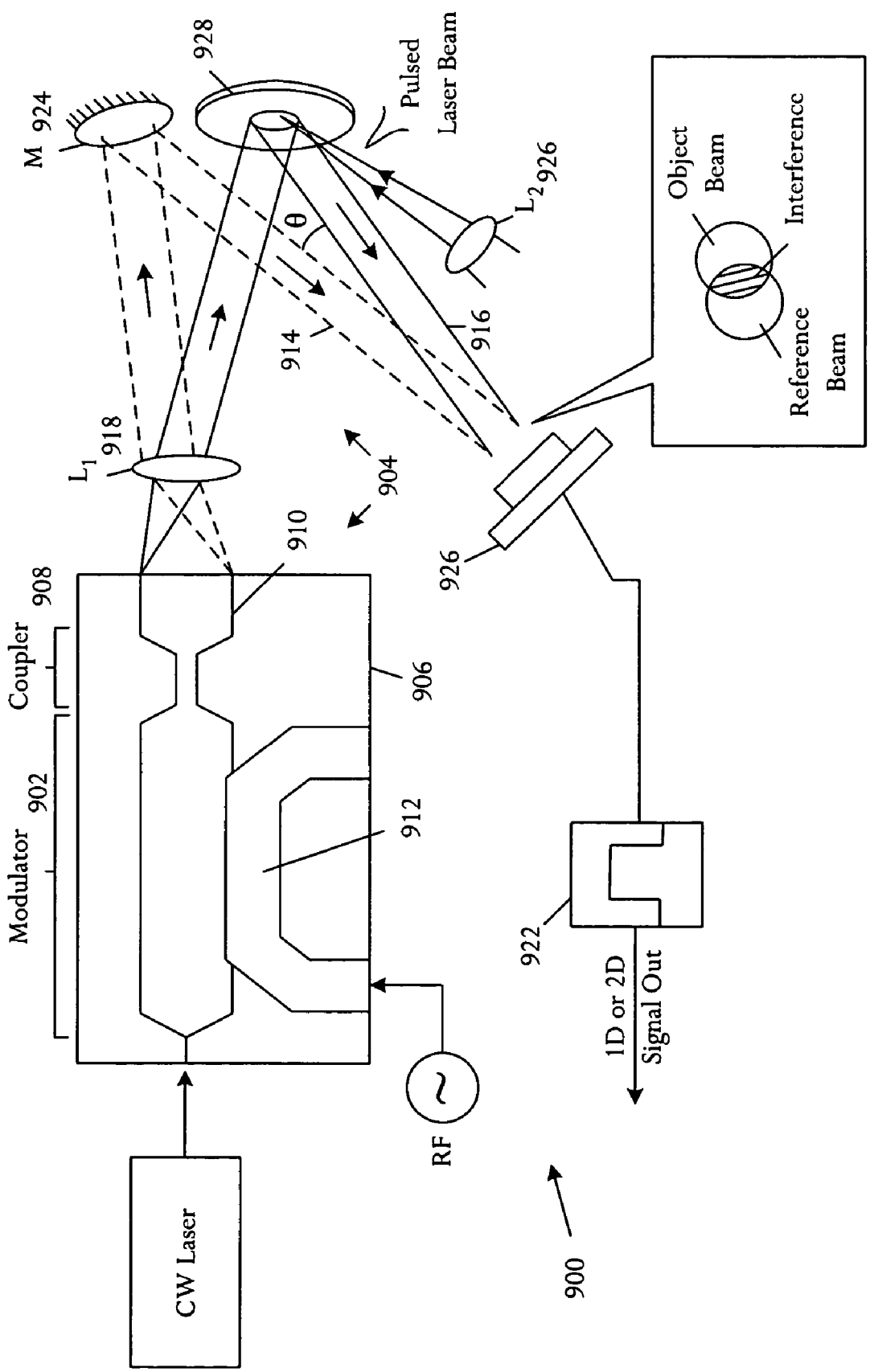
FIG. 9 is a schematic pictorial and block diagram illustrating an embodiment of a sensor that is particularly adapted for usage in detecting surface and subsurface defects.

Referring to FIG. 9, a schematic pictorial and block diagram illustrates an embodiment of a sensor 900 that is particularly adapted for usage in detecting surface and subsurface defects. The sensor 900 uses cascaded integrated electro-optic (EO) polymer Mach-Zehnder 902 and bulk-optic 904 interferometers. The sensor 900 detects pulsed laser-induced high-frequency acoustic resonance in a multi-layer system. The sensor 900 down-converts high-frequency (GHz) acoustic signals to low-frequency (kHz) detectable signals. The sensor 900 can produce either a single point defect signature, or a two-dimensional (2D) acoustic "image" that can indicate subsurface defects, for example delamination, thickness variation, cracks, inclusions, and damaged micro- or nano-structure. The sensor 900 can be used for two-dimensional (2D) detection by implementing an arbitrary angle of incidence detection technique.

The sensor may be described as a cascaded sensor 900 comprising an electro-optic device 906 including a Mach-Zehnder (MZ) modulator 902 and a coupler 908. The electro-optic device 906 includes optical waveguides 910 and a radio frequency (RF) electrode 912. The angle (θ) between reference 914 and object 916 beams can be adjusted to control fringe spacing, optimized for detector size. The sensor 900 further includes a collimating lens $L_1$ 918 is a collimating lens and a focusing lens $L_2$ 920. An electrical band-pass filter BPF 922 may be used to down-convert frequency of the detected signal. A reference mirror M 924 is used to form the reference beam 914. Photo-detector (PD) 926 can be either a single element or a two-dimensional (2D) array to enable interrogation of a single spot or a larger area, respectively. The photo-detector 926 active area is smaller than fringe spacing, or a pinhole can be used in front of the photo-detector 926. Focusing optics are not shown but may also be used for small spot interrogation.

Sensor 900 comprises two cascaded interferometers 902, 904. In an illustrative embodiment, the first interferometer is an active integrated optical interferometer which includes an electro-optic Mach-Zehnder modulator MZ 902. Following the modulator 902 is a second interferometer 904 which comprises a waveguide light coupler 908, a collimating lens $L_1$ 918, a reference mirror M 924, and a test sample 928 that reflects light to a photo-detector PD 926. The waveguide light splitter 910 is shown as a directional coupler 908 but may be replaced by another type of coupler such as a Y-junction coupler. The photo-detector PD 926 can be a single element or a two-dimensional photo-detector 2 DPD.

Phase modulation on the light caused by a vibrating surface in the sample 928, or due to elastic wave induced change in the refractive index near the sample surface, mixes with modulation due to the Mach-Zehnder modulator 902. A pulsed laser beam is generated by a laser that is not shown and is used to excite elastic waves in the sample 928.

The sensor architecture uses integrated optics as well as bulk or fiber optics. The multifaceted approach exploits the complementary aspects of the different optic technologies. The integrated electro-optic (EO) technology enables ultra-high frequency, gigahertz (GHz) range operation, which translates to high-resolution sensing. Bulk optics enables two-dimensional detection and arbitrary incident angle detection capabilities, avoiding the need to scan the sensor head, a very slow process. Furthermore, the multifaceted approach eliminates the need to couple light reflected from the sample back to a waveguide, which requires active alignment and may result in high optical losses and reduced sensor sensitivity. Combined integrated and bulk optics solves these problems in a cost effective manner.

Figure 10:
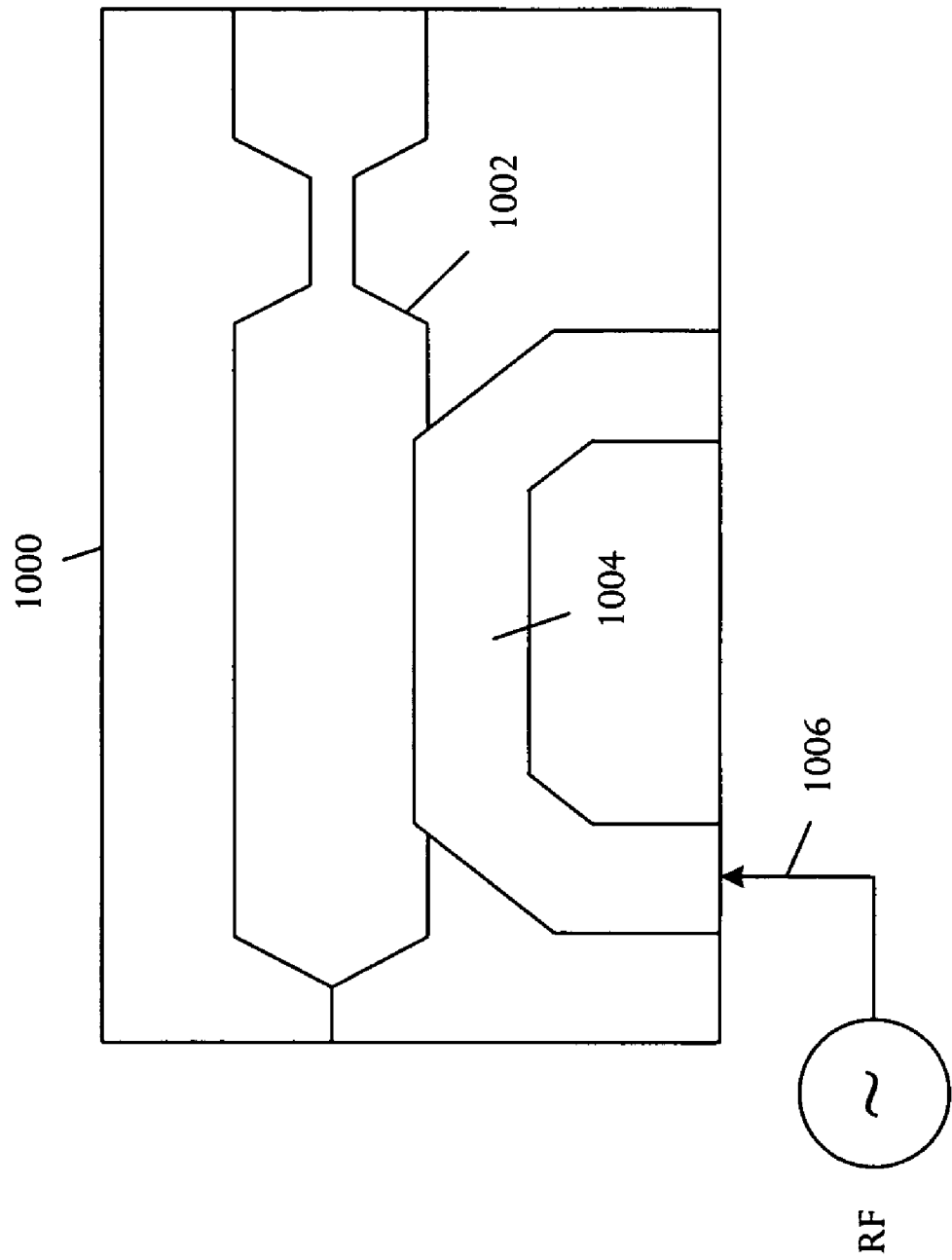
FIG. 10 is a schematic diagram depicting an embodiment of an electro-optic device that may be used in the architectures depicted in FIGS. 1, 5, 6, 8A-C, 9, 11A, 12, 13, and 14.

Referring to FIG. 10, a schematic diagram illustrates an embodiment of an electro-optic device 1000 that may be used in the architectures depicted in FIGS. 1, 5, 6, 8A-C, 9, 11A, 12, 13, and 14. The electro-optic device 1000 has channel or ridge waveguides 1002, and an electrical line 1004, such as a micro strip-line. The waveguide layers 1002 have an electro-optic (EO) layer of higher refractive index, surrounded by lower and upper cladding layers of lower refractive index. The index difference confines light in the vertical direction. Light guiding in the planar direction is enabled by introducing ridges in the electro-optic layer. Alternatively, channels can be etched in the lower cladding layer. The channel or ridge waveguide layers 1002 enable electro-optical functionality as a modulator. The device 1000 has an electrical line 1006 to transmit the radio frequency (RF) or microwave signal. In one example configuration, a micro strip-line 1004 is constructed as a metallic ground plane on which the waveguide layers 1002 are grown, and an upper electrode 1004 is patterned on top of the upper cladding layer. Alternatively, a coplanar line can be patterned above the upper cladding and can be used for RF/microwave transmission. Several techniques are available to fabricate waveguides and electrodes, including techniques using polymeric materials such as Lithium Niobate ($LiNbO_3$) or electro-optic polymers.

To fabricate the device 1000 using polymeric materials, upper and lower cladding layers constructed from optically clear epoxies are spin coated. The electro-optic layer is also spin-coated and poled to align the molecules, making the layer electro-optically active. In an optically-active material, refractive index changes when a voltage is applied across the layer. Poling can be done either via corona poling or contact poling. Waveguides 1002 are patterned using standard lithography methods, for example by spinning photo-resist and patterning the layer with a mask aligner. After waveguides 1002 are patterned onto a photo-resist, the ridge or channel waveguide pattern is transferred to the electro-optic or lower cladding layer using reactive ion etching (RIE). Similarly, the electrodes 1004 are patterned using standard lithography methods on top of a metal layer. The metal layer is coated on top of the upper cladding. A typical metal film is a gold (Au) film coated on top of an adhesion layer such as chromium (Cr). The photo-resist pattern can be transferred to the metal layer by wet etching.

Figure 11A:
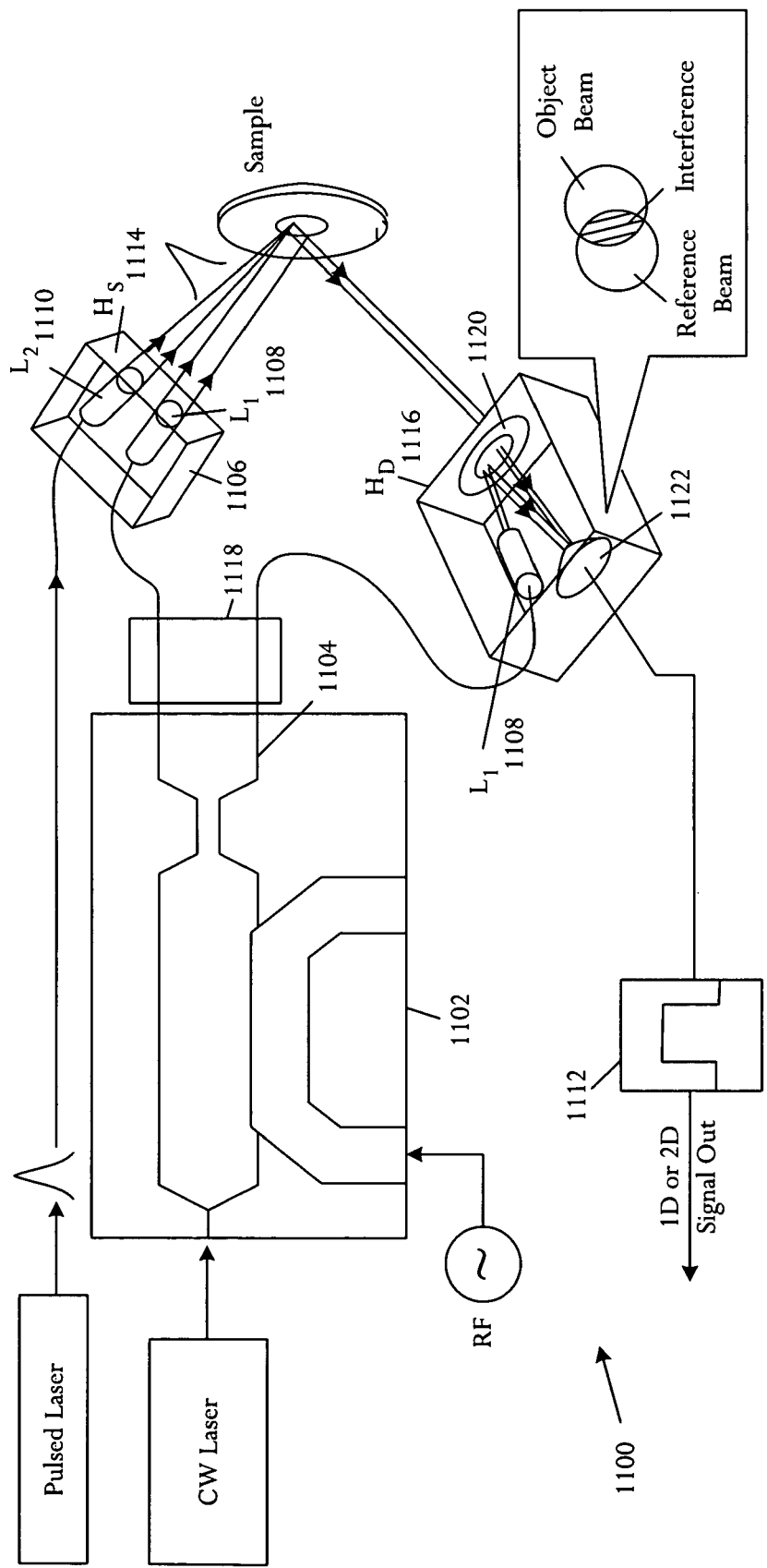
FIG. 11A is a schematic pictorial and block diagram illustrating an embodiment of an electro-optic sensor that is an alternative to the sensor architecture shown in FIG. 9 and is particularly adapted to use fiber light delivery.

Referring to FIG. 11A, a schematic pictorial and block diagram illustrates an embodiment of an electro-optic sensor 1100 that is an alternative to the sensor architecture shown in FIG. 9 and is particularly adapted to use fiber light delivery. Light from the output terminal of the waveguide 1104 of an integrated electro-optic device 1102 is coupled to a double fiber array 1106. Fiber delivery makes the sensor 1100 easily adaptable to various process instruments, for example to a mask aligner 1150 shown in FIG. 11B for detecting defects during lithography, and to process chambers 1170, such as a sputtering chamber depicted in FIG. 11C, for example to detect defects during metallizing or etching.

The alternative sensor architecture 1100 supplies a fiber-coupled output terminal. The double fiber array 1106 includes a fiber collimating lens $L_1$ 1108 and a focusing lens $L_2$ 1110. The sensor 1100 further includes an electrical band-pass filter BPF 1112, and respective source $H_S$ 1114 and detector $H_D$ 1116 heads. A fiber ribbon or V-groove 1118 can be used to transfer optical signals to the source $H_S$ 1114 and detector $H_D$ 1116 heads.

The detector head $H_D$ 1116 may include a fiber collimating lens $L_1$ 1108, a beam splitter 1120, and a photo-detector 1122, for example either a one-dimensional (1D) or two-dimensional (2D) photo-detector 1122.

Figure 11B:
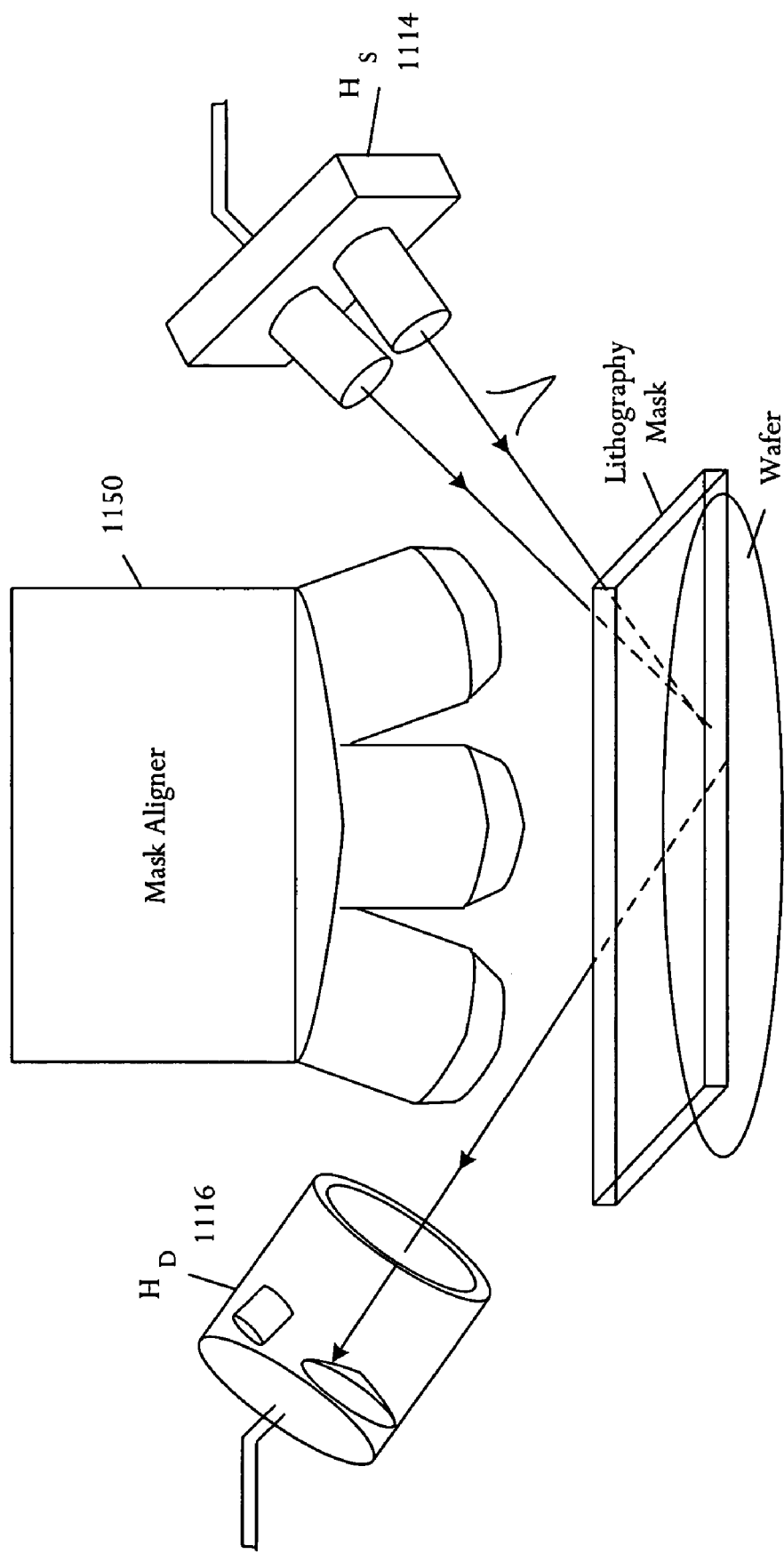
FIGS. 11B and 11C are pictorial diagrams illustrating applications of the sensor shown in FIG. 11A for real-time defect identification.
Figure 11C:
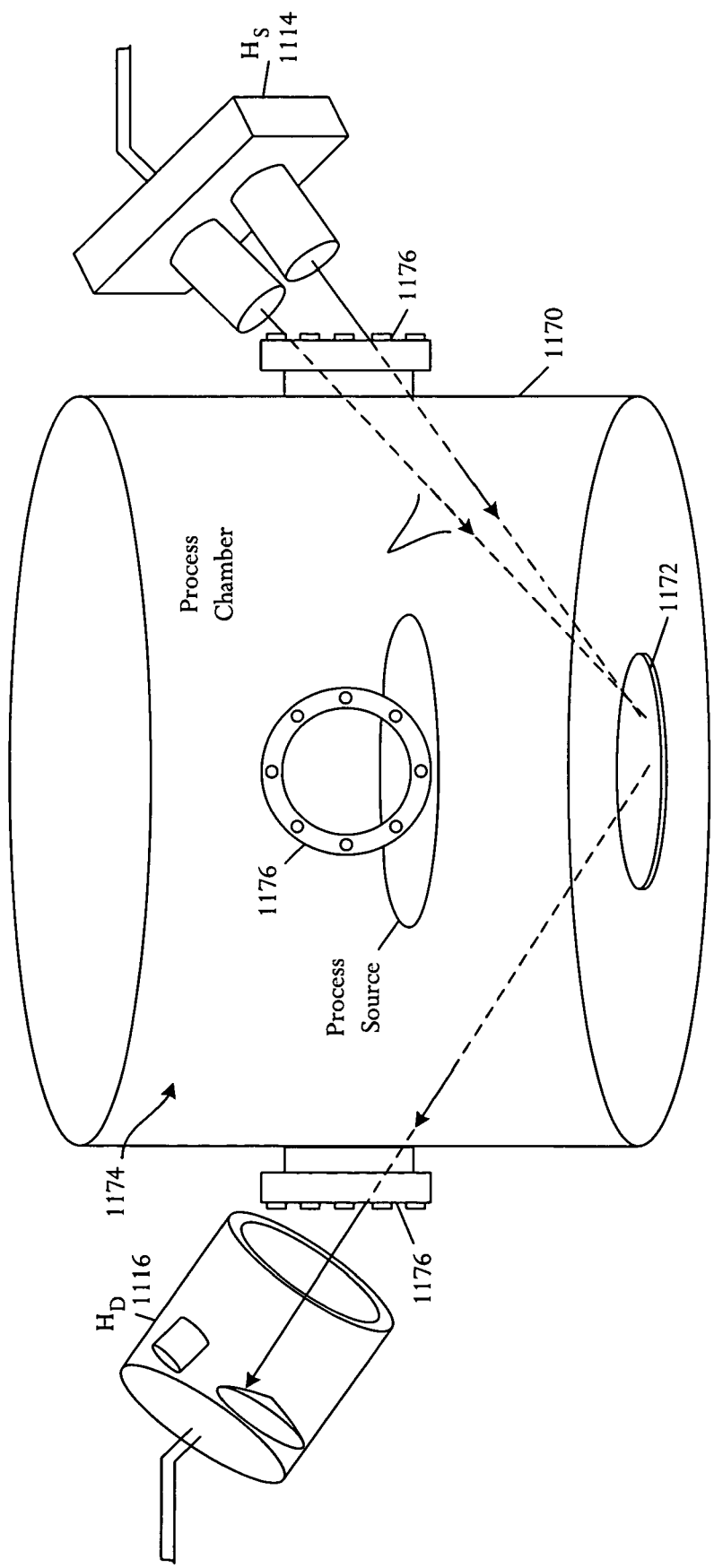

FIGS. 11B and 11C illustrate applications of the sensor 1100 for real-time defect identification in conjunction with a lithography apparatus, such as a mask aligner 1150 in FIG. 11B, and for usage in FIG. 11C while a sample 1172 is in a process chamber 1170, for example during sputtering or reactive ion etching. The chamber interior 1174 can be accessed from chamber windows 1176. Even if one window is available for access, a mirror can be mounted inside the chamber to direct light reflected from the sample out of the window and to the detector head $H_D$ 1116.

Figure 12:
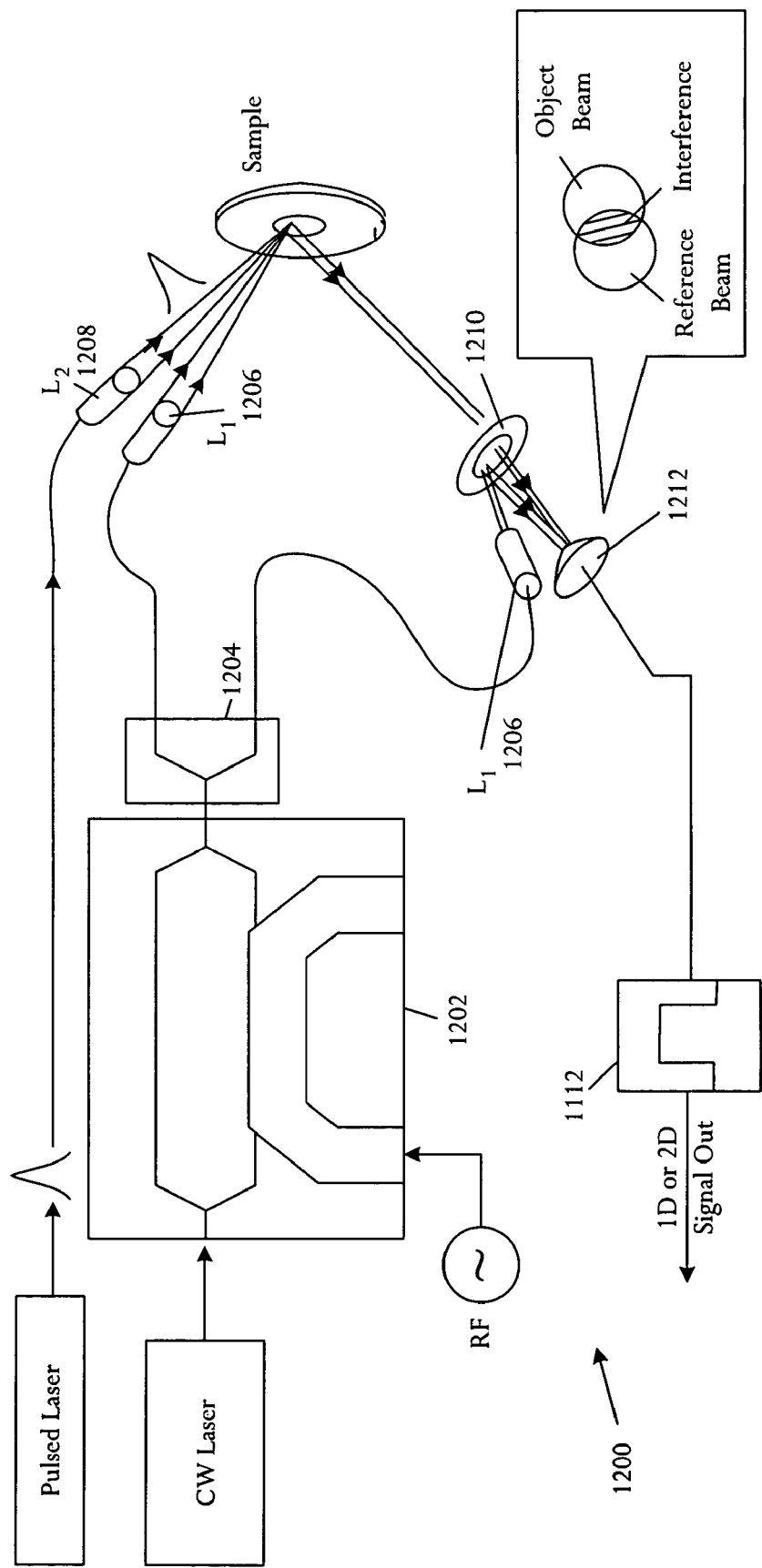
FIG. 12 is a schematic combined pictorial and block diagram showing an embodiment of a sensor architecture that uses an amplitude modulator followed by a fiber coupler.
Figure 13:
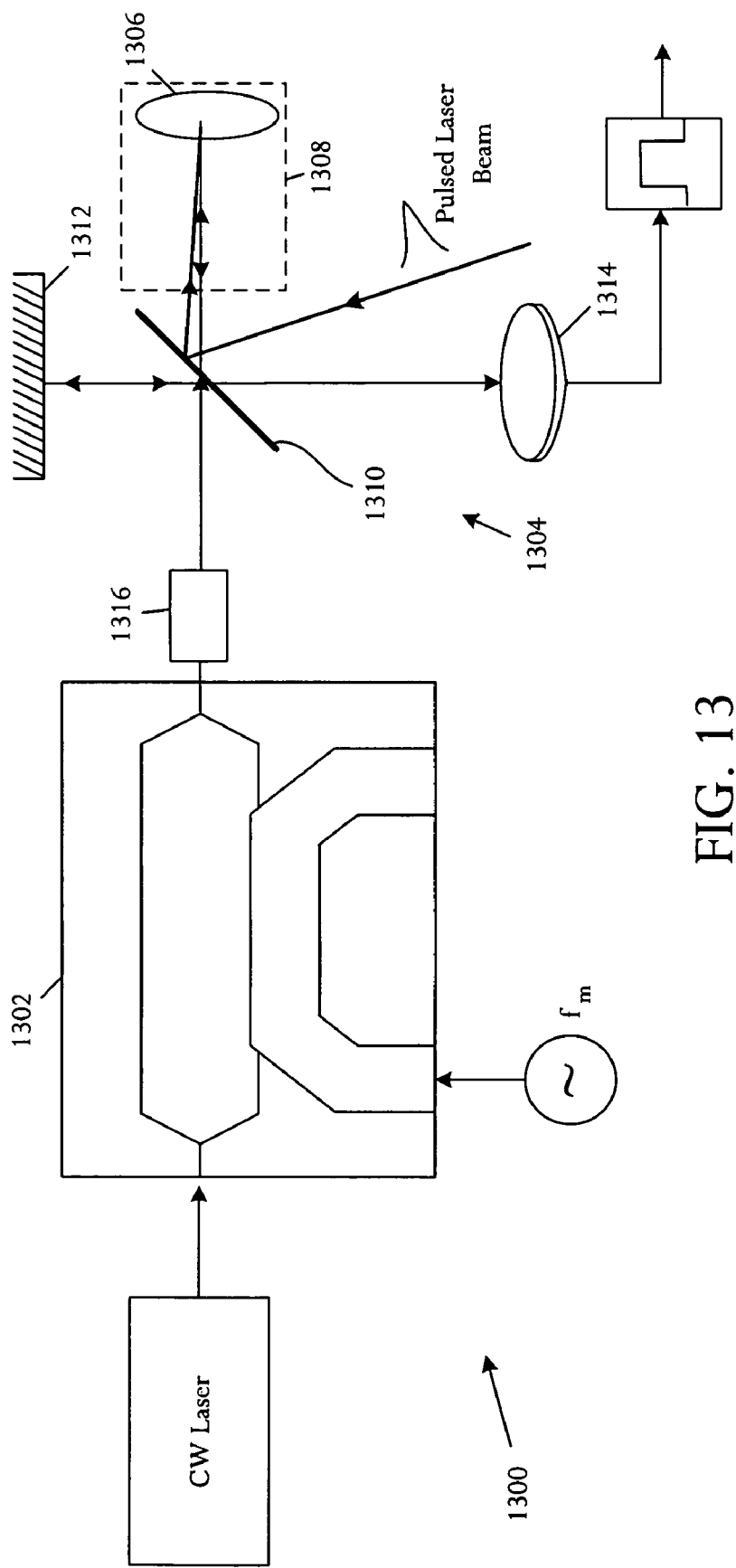
FIG. 13 is a schematic combined pictorial and block diagram showing an embodiment of an alternative sensor architecture including an electro-optic modulator followed by a bulk optic Michelson interferometer.
Figure 14:
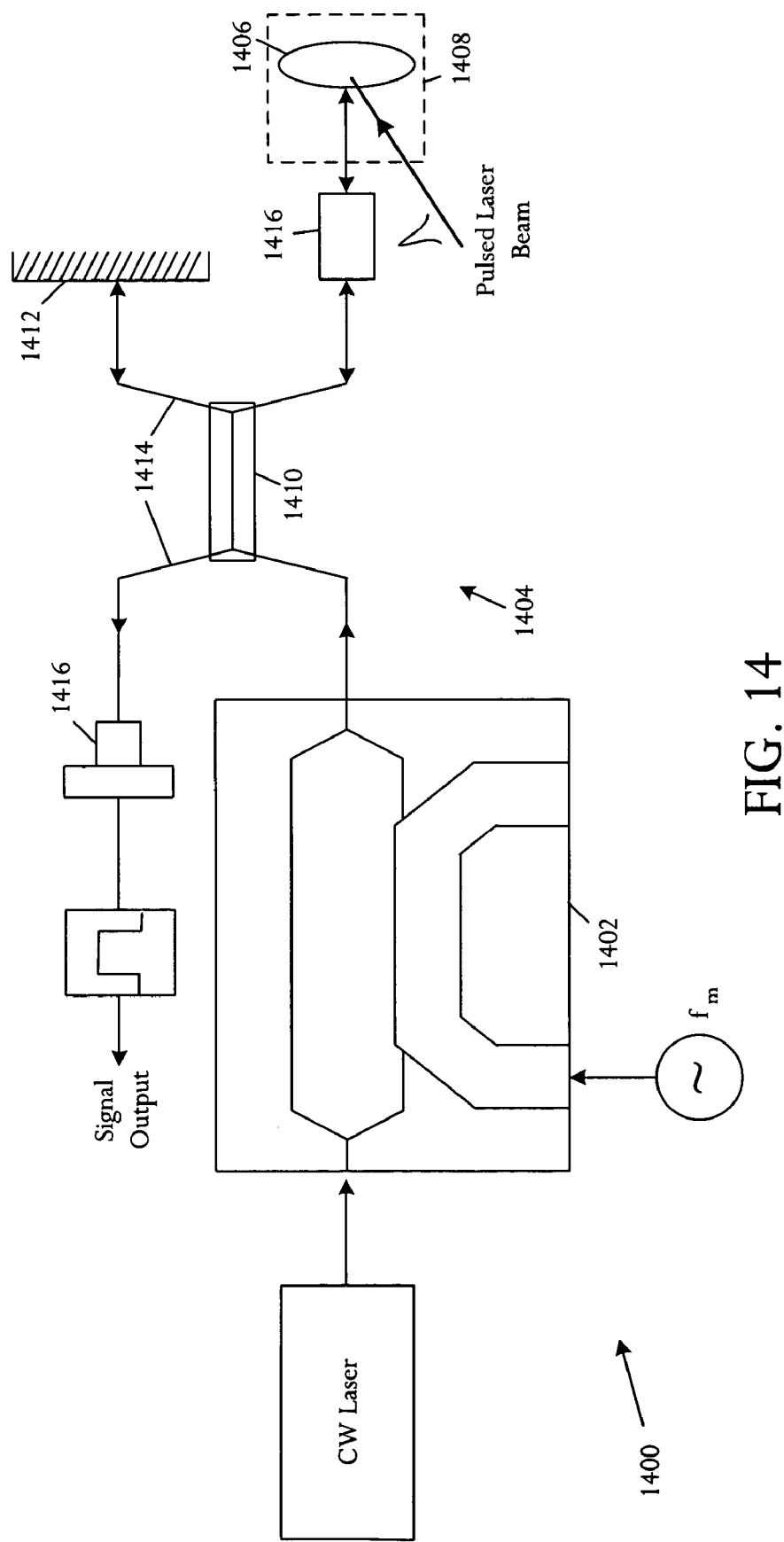
FIG. 14 is a schematic combined pictorial and block diagram showing an embodiment of an alternative sensor architecture including an electro-optic modulator followed by a fiber-optic Michelson interferometer.

Referring to FIGS. 12, 13, and 14, several schematic pictorial diagrams illustrate embodiments of sensors using alternative architectures. FIG. 12 shows a sensor architecture 1200 that uses an amplitude modulator 1202, shown as a Mach-Zehnder modulator although other technologies such as an electro-absorptive modulator may be used. A 1×2 (50:50 split) fiber coupler 1204 is connected after the modulator 1202. The sensor architecture 1200 enables implementation using off-the-shelf components, for example including fiber collimating lenses $L_1$ 1206, focusing lens $L_2$ 1208, beam splitters 1210, and a single point or a one-dimensional (1D) or two-dimensional (2D) photo-detector 1212.

Sensor architectures 1300 and 1400, shown respectively in FIGS. 13 and 14, use a modulator 1302, 1402 followed by a bulk optic 1304 or fiber-optic 1404 Michelson interferometer. In both cases, a probe beam is normal to the sample 1306, 1406. Focusing optics, although not shown, can be used to focus a pump beam, as well as the probe beam, on the sample 1306, 1406. The "pump" laser beam, which can be termed a "generation beam", is a pulsed beam that excites the sample for analysis. The "probe" beam from the sensor detects vibration and enables analysis of the acoustic spectra. Focusing optics can also be used as part of a microscope attachment. The focusing and imaging optics 1308, 1408 are generally placed near the sample 1306, 1406.

Referring to FIG. 13, the alternative sensor architecture 1300 has an electro-optic modulator 1302 followed by a bulk optic Michelson interferometer 1304. Laser illumination on a pulsed laser beam path is directed to a beam splitter 1310 and then through focusing and imaging optics 1308 to the sample 1306. A reference mirror 1312 reflects the reference beam through the beam splitter 1310 to a single element or two-dimensional photo-detector 1314.

Referring to FIG. 14, the alternative sensor architecture 1400 uses an electro-optic modulator 1402 followed by a fiber-optic Michelson interferometer 1404. Laser illumination on a pulsed laser beam path is directly applied to the sample 1406 through the focusing and imaging optics 1408. The illustrative fiber-optic Michelson interferometer 1404 further includes a 2×2 fiber coupler 1410, optical fibers 1414, a reference mirror 1412, such as a fiber reflector, and photo-detector 1416.

In some cases the pulsed laser can be tightly focused with a high power microscope objective lens to generate high enough light intensity to excite elastic waves. A long working distance microscope objective may be used to focus the pulsed laser at a selected angle. Alternatively, standard microscope objectives with a short working distance may be sufficient in a system that includes nearly co-linear beams, for example a pulsed laser, and probe beams. If a standard objective is used, the microscope objective focuses the pump as well as the probe beam onto the sample which is placed at or near the focal point of both beams. A collimating lens 1316, 1416 may be included in the sensor 1300, 1400, respectively, so that a collimated probe beam focuses onto the sample and the return reflection is re-collimated on traveling back through the objective lens. The microscope objective lens can also serve to image the sample, which is useful to visualize the location of the pump and the probe beam illumination. Simultaneous imaging of the sample is enabled by adding a microscope eyepiece to the arrangement when using either long or short working distance microscope objectives.

Other embodiments include variations to the illustrated device architectures. For example, the modulator of the illustrative device structures can extend to other than the Mach-Zehnder architecture. The depicted modulators may alternatively use an electro-absorption modulator, a polarization modulator, or a directly-modulated laser for modulating light in place of external modulation. Examples of a polarization modulator may include an electro-optic modulator configured as a straight channel waveguide, or a bulk crystal, with input and output polarizers. The modulator selection depends on the application since individual modulators vary in bandwidth and frequency response.

When a pulsed laser, typically $10^{-12}$s to $10^{-15}$s in pulse width, impinges upon a single or multi-layer structure, a shock wave is generated that propagates in the material. Two acoustic excitation modes can be used in conjunction with the illustrative sensors. A first method detects a surface vibration signature of a micro or nano structure. A second method measures strain-induced refractive index change near the surface of the sample under test. Various sensing may be used with any of the illustrative sensors.

In some embodiments, a method of acquiring subsurface structural information comprises illuminating a sample under test with a pulsed laser signal that propagates a shock wave through the sample and measuring a surface vibration signature of a micro or nano structure of the sample induced by the pulsed laser signal.

Figure 15B:
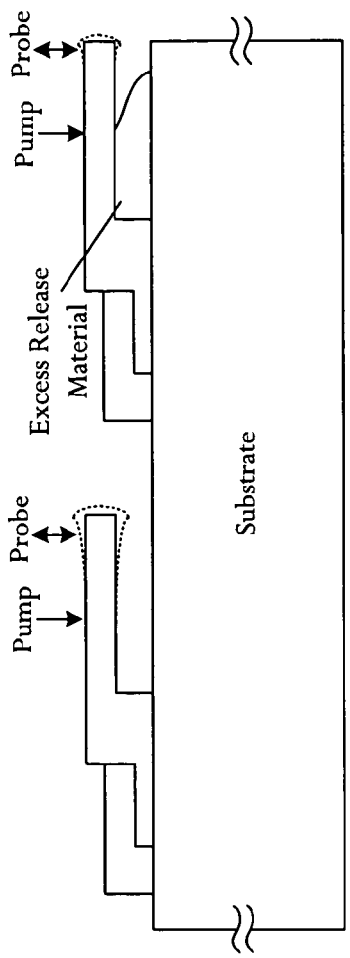
FIGS. 15A and 15B are pictorial views respectively depicting two types of defects that can be detected by evoking and detecting surface vibration of a sample.
Figure 15A:
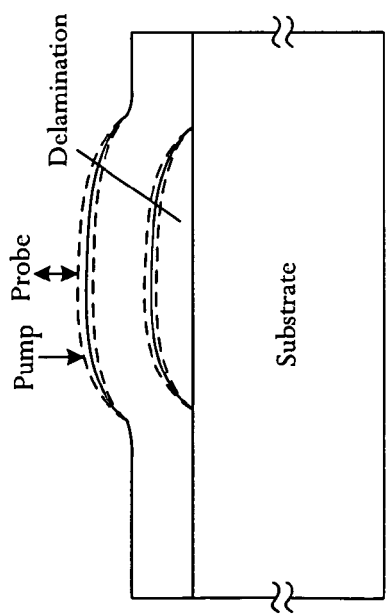

FIGS. 15A and 15B are pictorial views depicting two types of defects that can be detected by evoking and detecting surface vibration of a sample. The illustrative sensors can be used to detect defects in a single layer or a last layer of a multi-layer structure, such as delamination as shown in FIG. 15A. A delaminated film resonates when excited with a pulsed laser and the measured vibration spectrum yields information about the size and severity of delamination. Resonance can be detected by analyzing the surface vibration of the sample using the various illustrated sensor architectures. A delaminated layer mechanically resonates at a specific frequency when excited with a pulsed laser. Probe beam from the sensor detects surface vibration and enables analysis of the acoustic spectra.

Referring to FIG. 15B, a micro-electromechanical systems (MEMS) cantilever resonates at a specific frequency when excited with the pulse laser. The left portion illustrates a properly released structure. The right portion depicts an improperly released structure with excess release material. The resonance frequency and the amplitude of the properly and improperly released cantilevers differ and can be measured.

The pulsed laser is excited, causing the micro-electro mechanical (MEMS) cantilever structure to resonate. Individual MEMS structures have a characteristic spectrum. When defects are present, such as micro-cracks, delamination, or excess material, the characteristic spectrum changes, thus yielding information about the defect.

In accordance with other embodiments, a method of acquiring subsurface structural information comprises illuminating a multiple-layer sample under test with a pulsed laser signal that excites elastic waves propagating normal to a sample surface, reflecting from multiple-layer surfaces back to the surface. The method further comprises measuring changes in refractive index near a surface of the sample under test induced by the pulsed laser signal.

The sensors depicted hereinabove can also be used to detect defects in a multi-layer structure. In contrast to the method of detecting surface vibrations, a change in the refractive index near the surface of the sample is detected and analyzed. A pulsed laser is used to excite elastic waves that propagate normal to the surface, reflecting from multi-layer interfaces, and are reflected back to the surface. Differences in elastic wave velocities between adjacent layers cause acoustic reflection. Reflected elastic waves travel back to the near surface. The strain induces a small change in the refractive index ($\Delta n$) as well as change in absorption ($\Delta \alpha$) near the surface as shown in FIG. 16A. The change in refractive index $\Delta n$ carries information about the multiple-layer structures.

Light from of the sensor enters the top layer and part of the light is reflected from the first layer, as well as other layers. The reflected light is phase modulated due to changes in refractive index ($\Delta n$). The phase modulation is mixed with the electro-optic modulation signal and down-converted to a low frequency signal.

FIG. 16A illustrates a pictorial view of a cross section of a multi-layer sample with embedded structure. The sample can be interrogated by observing the pulsed laser induced strain which causes change in the refractive index near the surface. The illustrative multiple-layer sample has several defects. Region (i) is defect-free. Region (ii) contains delaminated layers. Region (iii) contains internal cracks. Region (iv) contains microstructures, some of which are damaged during processing. Arrows indicate direction of elastic pulse propagation.

Figure 16B:
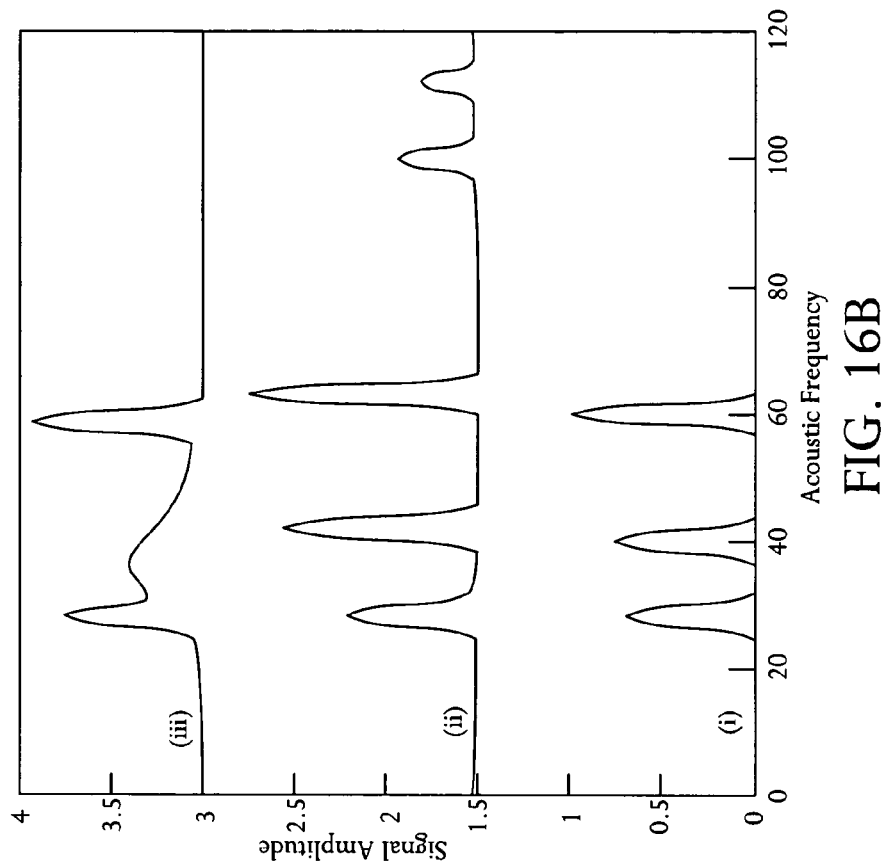
FIGS. 16A and 16B respectively show a pictorial view of a cross section of a multi-layer sample with embedded structure, and a schematic graph illustrating an expected acoustic spectrum when the material in the sample is interrogated.
Figure 16A:
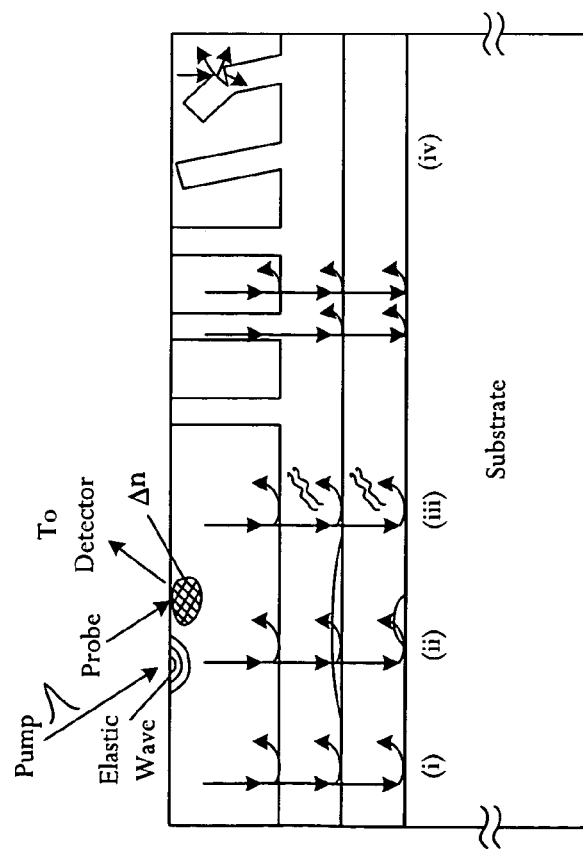

FIG. 16B is a schematic graph that illustrates an expected, for example hypothetical curve, high-frequency acoustic spectrum when the material is interrogated in regions i, ii, and iii. Frequency range of the spectrum depends on layer thickness and is generally in the range of tens of gigahertz (GHz) or higher for micron/sub-micron thick layers.

A multi-layer structure has a characteristic spectrum and any damage and defect, such as delamination of the layer, internal-cracks, thickness variation, or the like, result in a change in the spectrum. Hypothetical spectra are shown in FIG. 16B. A normal spectrum is shown in the lower graph relating to region (i). Deviation of the normal spectrum shown in region (i) is expected due to delamination as shown in the middle graph of region (ii). The spectra resulting from micro cracking is shown in the top graph relating to region (iii).

Delamination and changes in layer thickness result in shift of the spectral resonances and appearance of additional resonances. Internal cracks result in acoustic loss and spectral broadening. Similarly, defective micro or nano structures also result in an altered spectrum of various types relating to region (iv) that is not shown.

Layer thicknesses in VLSI circuits, MEMS or photonic integrated structures are on the order of microns or submicrons. Resonant frequencies are in the range of tens of gigahertz (GHz) or higher. Film feature analysis in real time involves analyzing acoustic resonance at the high frequencies which are outside the detection range of piezoelectric transducers. Direct detection of interferometer output signals typically is performed by photo-detectors and electronics operating in the range of tens of gigahertz (GHz) so that suitable systems include high-sensitivity and high frequency sensors. The highest sensitivity is generally achieved using optical interferometry. One problem associated with detection of GHz-range optical signals is a lack of high gain, low noise photo-detectors and electronics at the high frequencies. Accordingly, what is desired is to down-convert GHz optical signals to lower frequencies to enable usage of detectors that are less noisy and have higher gain.

Acoustic excitation using the illustrative methods can be implemented using the same sensor and similar optical setup without having to change instrumentation, enabling a wide range of defect detection capabilities using a single sensor configuration. Either the pump laser or the probe laser, or both, can interrogate at a single wavelength or multiple wavelengths. Accordingly, the sensor can be used to interrogate a wide range of multi-layer semiconductor materials. Appropriate selection of probe and pump wavelengths can improve or optimize detection sensitivity.

INSTRUMENT CALIBRATION AND SPECIFICATION

The illustrative methods are most effective for a sensor that is suitably calibrated to enable detected defects to be quantified. A calibration technique is as follows.

An end user enters multiple-layer film parameters before starting the process. As shown in FIG. 2, the processing electronics and data display allow entry of parameters including specification of materials, layer thickness, deposition speed (Angstroms/s), and the like. Layer parameters values such as acoustic velocity, density, absorption coefficient, and the like can be extracted from a look-up table. A computer model calculates the expected spectrum, a spectrum that varies in time as layers are grown.

The spectrum is scanned to DC and a peak value is observed at the lower frequency end of the spectrum. The peak results from cos $(2\omega_m t)$ term in Equation (2) when $2\omega_m$ falls within the band-pass filter bandwidth. The peak value can be used to obtain a vibration amplitude. When $\phi_m = 2\phi_s$ the observed spectrum contains two peaks of the same height. One peak is at the vibration frequency. The second peak is near DC. Knowledge of electro-optic modulation amplitude, $\phi_m$, which is known from device parameters, yields the vibration amplitude.

The relative phase difference between multiple resonances can also be obtained from the shape of the recorded spectrum. The shape of the beat signal depends on the phase of the acoustic resonance. Observation of shape differences between two resonant peaks yields information on their relative phase difference. To illustrate the shape differences, four different resonant peaks are simulated with relative phases are set to 0, $\pi/4$, $\pi/2$, and $\pi$, as shown in FIG. 17.

Figure 17:
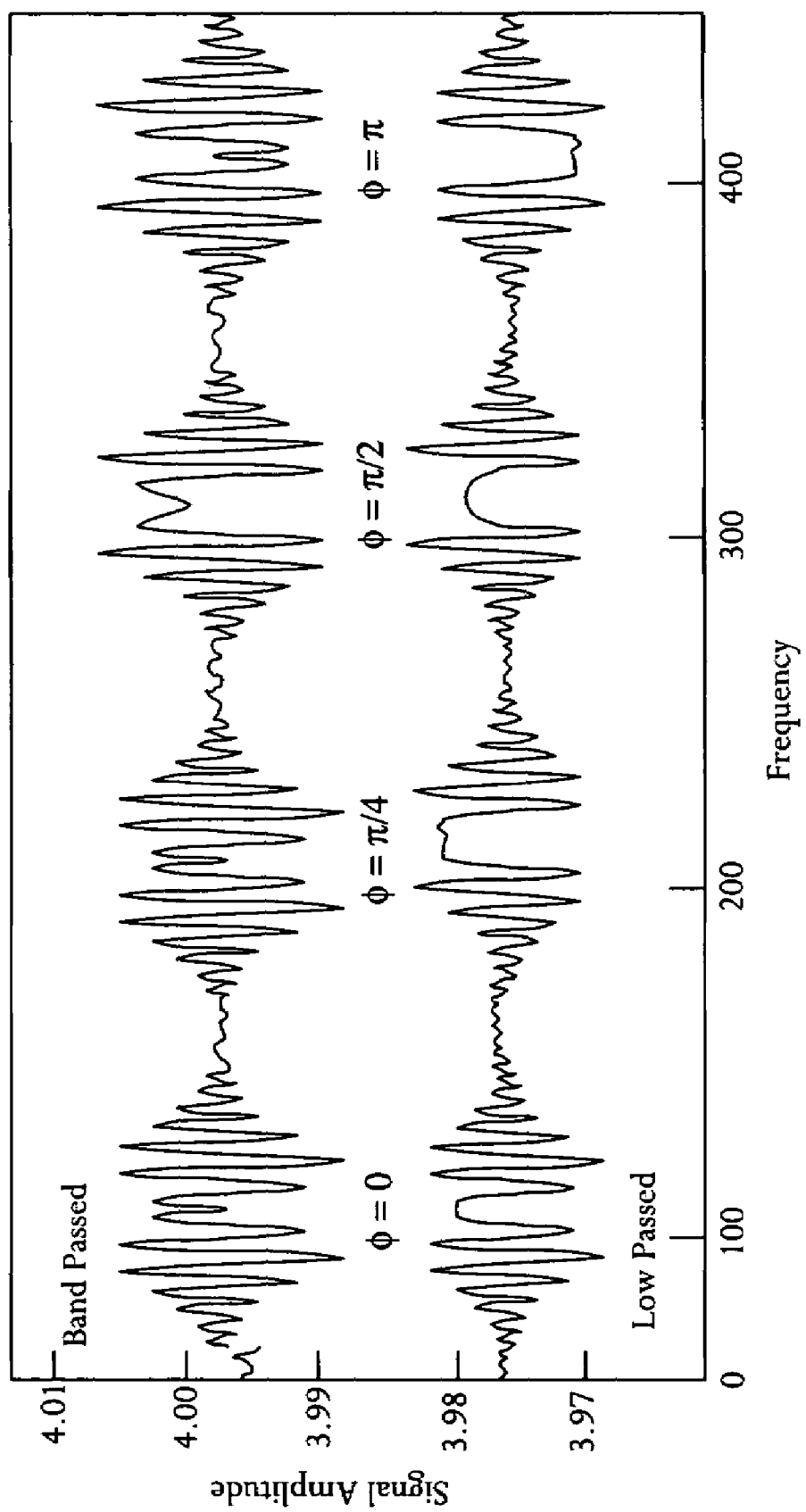
FIG. 17 is a spectral graph showing examples of spectra that may be acquired during testing.

FIG. 17 is a spectral graph showing examples of spectra that may be acquired during testing. Relative phase difference is determined between the resonances from the shape of the spectrum using the described detection methods. The top graph shows simulation using band-pass filtering. The lower graph shows a simulation using a low-pass filter geometry.

FIG. 17 shows that the shape of the signal depends on the phase. For example, the central lobe of the low-passed signal points upward for $\phi=0$. Delaying the phase of the resonance by $\pi$ results in the central lobe pointing downward. By determining both the phase and the amplitude of vibrations, the time domain signature can be obtained by inverse Fourier transformation. Experimental data can be compared to the theoretical time signature.

Figure 18:
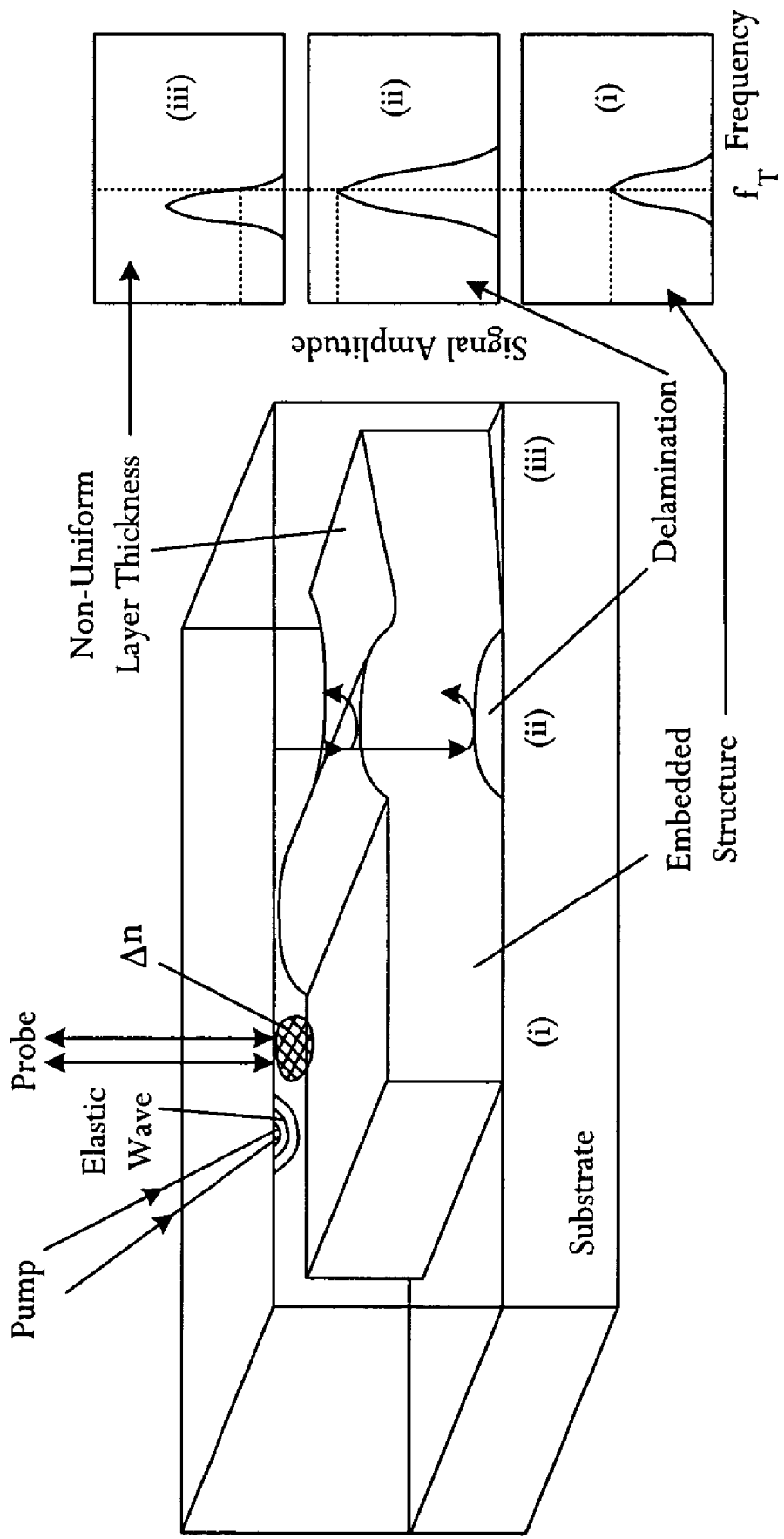
FIG. 18 is a schematic pictorial view depicting an example of a sample under test using another embodiment of a testing method.

Referring to FIG. 18, a schematic pictorial view shows an example of a sample under test using another embodiment of a method of detecting strain-induced refractive index change by detecting shift of acoustic resonance. In the illustrative example, the elastic wave generation and detection method distinguishes three regions. Region (i) is a normal or desired structure. Region (ii) shows a delaminated layer. Region (iii) illustrates a thickened structure. Acoustic resonance spectra are shown for regions (i) to (iii).

The method includes acoustic excitation and detection. A pulsed laser, called a pump, is used to excite elastic waves that propagate normal to the sample surface and reflect from multiple-layer interfaces. The strain induced by the elastic wave changes the optical properties near the surface. Both refractive index ($\Delta n$) and absorption ($\Delta \alpha$) are modulated. The signal carries information about the multi-layer system, for example layer density, sound velocity, and thickness. The signal also contains information relating to presence of defects such as improper adhesion gaps, and the like. Light from the sensor, called the probe, enters the top layer. Part of the light is reflected from the first layer and other layers. The reflected light is phase modulated by the strain-induced refractive index $\Delta n$. The refractive index $\Delta n$ is mixed with the electro-optic modulation signal and down-converted to a low frequency signal. The entire structure may also vibrate or surface waves may be present. The structural vibration and surface waves resonate at much lower frequencies than the frequency of modulation of the refractive index $\Delta n$ due to the multi-layer structure. Therefore a high-frequency spectrum yields information about the subsurface thin film structure. This technique is applicable even with "opaque" films, such as thin metals and semiconductors, since some light always penetration in the film. Various wavelengths can be used to optimize depth penetration for a specific multi-layer system.

One application of the sensing method is interrogation of subsurface structure for lithography applications. During lithographic growth of layered structures, visualization of subsurface structures, alignment marks, and embedded defects is useful to enable reduction of fabrication errors. Defects, such as small variations of the layer thickness and delamination, are not easily detected visually or by visualization using a charge-coupled device (CCD) camera or other type of camera. Furthermore, if the upper layer is opaque or has low transmission in the visible wavelengths, alignment marks are very difficult to see. The illustrative method enables visualization of subsurface structures and defects.

FIG. 18 illustrates a subsurface layer with an ideal structure in Region (i), delaminated in Region (ii), and has thickness variation in Region (iii). The corresponding acoustic spectrum of Region (i) is shifted and thus different from the spectrum of Region (iii) because acoustic resonance is dependent on the layer thickness. Region (ii) has a different acoustic signal amplitude than region (i) due to a different reflection coefficient at the delamination interface. When the electro-optic modulator frequency is tuned to the embedded structure resonance, for example to Region (i), the sensor display shows most of the embedded structure with a single color (or gray level). Delamination or thickness variation results in change in the amplitude of the acoustic signal with resonance curve amplitudes marked as shown. A different colored region can be shown on an image screen. The resulting color-coded image on the instrument display reveals thickness variations and delaminations. Alignment marks are also made visible.

The disclosed method can use both integrated as well as bulk optics interferometers. Bulk interferometric systems generally need vibration isolation, which will be problematic in the industrial settings. However the sensors and methods disclosed herein do not require vibration isolation because the techniques use frequency domain interrogation with modulation frequencies in the GHz range and down-conversion to frequencies in the high kHz range. Typical room vibrations occur at frequencies less than 100 Hz, far below the frequencies used in the illustrative method.

The illustrative sensors can be used with detection methods other than those specified herein. Additional methods include but are not limited to detection using nonlinear elastic response at high frequencies and detection of anisotropy using surface acoustic waves.

Damage assessment can be made by examination of the nonlinear elastic response of the material. Damaged materials are well-known to exhibit higher non-linear elasticity than non-damaged materials. The nonlinear response yields higher harmonic acoustic resonances as well as generation of sum and difference acoustic frequencies. For example, if a thin film structure has two resonances and if the acoustic intensity is increased by varying the pump laser power, then sum and difference frequencies can be observed if the material exhibits quadratic nonlinearity.

The illustrative sensors can also be used to assess anisotropy near the sample surface. Acoustic excitation causes surface waves to be excited. For best directionality, the pulsed laser beam can be focused in a line using a cylindrical lens. The sensor can be placed to enable detection of surface vibrations a little further from the excitation region. By rotating the sample with respect to the sensor/pulse laser, or vise versa, the acoustic response changes if the sample exhibits anisotropy on or near the surface. For example, acoustic velocity is different at different angular orientations due to stress or due to anistropic defects such as cracks having a preferred orientation.

Different devices can be used with different methodologies. The illustrated device architectures can be variably used with the various illustrative methodologies. Specifically, any of the device architectures can be used to detect surface vibrations to interrogate single layer thin films or to interrogate subsurface layers, defects, inclusions, and the like using strain induced refractive index changes. Furthermore, any of the device architectures can be used either in acoustic spectrum analysis configuration, specifically by scanning the RF frequency to sweep the acoustic spectrum or by using a single frequency detection and comparing the acoustic response from various parts of the sample. If a two-dimensional photodetector is used, images can be formed and visualized without spatial scanning. Alternatively, if the sensor illustrated in FIG. 1 is used to detect strain-induced refractive index change by detecting a shift in acoustic resonance, then the signals produced by the photo-detectors are compared. For a larger area scan, the entire sensor head or the sample are spatially scanned.

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims.

What is claimed is:

1. A sensor comprising:
   two closely-coupled parallel active interferometers comprising:
      an optical modulator that generates a modulation signal; and
      an interferometer that mixes an acoustic signal evoked by a pulsed laser with the modulation signal to down-convert the acoustic signal to lower frequencies; and
   a photodetector coupled to the two closely-coupled parallel active interferometers that detects the down-converted signal.

2. The sensor according to claim 1 wherein the optical modulator and interferometer further comprise:
   two closely-coupled parallel Michelson interferometers, each having two interferometer arms and each Michelson interferometer being biased at zero phase difference between the two interferometer arms.

3. The sensor according to claim 1 wherein the optical modulator and interferometer further comprise:
   closely-coupled interferometers including a 50:50 directional coupler for beam splitting.

4. The sensor according to claim 1 further comprising: integrated closely-coupled waveguide device interferometers further comprising:
   a substrate;
   a metallic ground plane;
   waveguide layers comprising a lower cladding, an upper cladding, and a core layer between the lower and upper cladding layers, the core layer having a higher refractive index than the cladding layers that confines light according to ridge or channel waveguides etched into the core layer and/or one or more of the cladding layers; and
   a reflective-coated endface operative as a reference mirror on a first end of the waveguide device; and
   input/output optics coupled to a second end of the waveguide device opposite the first end and operative to reflect light back from a surface or from near a surface of a sample under test.

5. The sensor according to claim 1 wherein:
   the photodetector combines the acoustic signal and the modulation signal;
   at a zero bias point the interferometer has a quadratic response; and
   phase modulation on light caused by a vibrating surface of a sample or caused by an elastic wave-induced change in refractive index near a surface of the sample mixes with phase modulation generated by the optical modulator.

6. The sensor according to claim 1 wherein:
   the acoustic signal is in a gigahertz range and is down-converted to a kilohertz to megahertz range for detection by the photodetector which detects signals in the kilohertz to megahertz range.

7. The sensor according to claim 1 further comprising:
   a filter coupled to the photodetector and capable of filtering selected frequencies, the filter being selected from a low-pass homodyne filter or a band-pass heterodyne filter.

8. The sensor according to claim 1 wherein:
   the photodetector is a single element for one-dimensional, single-point detection.

9. The sensor according to claim 1 wherein:
   the photodetector is a two-dimensional array of elements for two-dimensional detection.

10. The sensor according to claim 1 wherein the optical modulator and interferometer further comprise:
    an amplitude modulator; and
    a bulk optic or fiber-optic Michelson interferometer in a configuration to form a probe beam normal to a sample and using focusing optics to focus a pump beam on the sample.

11. The sensor according to claim 1 further comprising:
    a pulsed laser coupled to evoke an acoustic signal through the interferometer.

12. The sensor according to claim 11 further comprising:
    a microscope objective lens coupled to focus light generated by the pulsed laser.

13. The sensor according to claim 1 wherein:
    the optical modulator is selected from a group consisting of a Mach-Zender modulator, an electro-absorption modulator, a polarization modulator, internal modulation of a direct-modulated laser, and an electro-optic modulator configured as a straight channel waveguide or bulk crystal with input and output polarizers.

14. A sensor comprising:
    an optical modulator that generates a modulation signal;
    a cascaded interferometer that mixes an acoustic signal evoked by a pulsed laser with the modulation signal to down-convert the acoustic signal to lower frequencies; and
    a photodetector that detects the down-converted signal.

15. The sensor according to claim 14 wherein the optical modulator and interferometer comprise:
    a cascaded active/passive interferometer.

16. The sensor according to claim 14 wherein the optical modulator and interferometer further comprise:
    an active integrated optical interferometer cascaded with a bulk optic interferometer that are operative whereby phase modulation on light evoked by a vibrating surface or due to elastic wave-induced change in refractive index near a sample surface mixes with phase modulation generated by the integrated optical interferometer.

17. The sensor according to claim 14 wherein the optical modulator and interferometer further comprise:
an active integrated optical Mach-Zender modulator cascaded with a bulk optic Michelson interferometer that are operative whereby phase modulation on light evoked by a vibrating surface or due to elastic wave-induced change in refractive index near a sample surface mixes with phase modulation generated by the integrated optical modulator.

18. The sensor according to claim 14 wherein the optical modulator and interferometer further comprise:
an active integrated optical interferometer cascaded with a two-beam interference operative whereby the two-beam interference includes a signal beam of light reflected from a sample surface or near a surface and a reference beam.

19. The sensor according to claim 14 wherein the optical modulator and interferometer further comprise:
an active integrated optical interferometer cascaded with a two-beam interference formed by one or more collimating lenses, the integrated optical interferometer and the two-beam interference being operative whereby the two-beam interference includes a signal beam of light reflected from a sample surface or near a surface and a reference beam.

20. The sensor according to claim 14 wherein the optical modulator and interferometer further comprise:
an active integrated optical interferometer cascaded with a two-beam interference formed by one or more collimating lenses, the two-beam interference further comprising:
a fiber coupler coupled to receive and split a modulated output signal from the active integrated optical interferometer; and
a beam splitter coupled the fiber coupler to recombine the split modulated signal.

21. The sensor according to claim 14 wherein the optical modulator and interferometer further comprise:
an active integrated optical interferometer cascaded with a two-beam interference formed by one or more collimating lenses, the two-beam interference further comprising:
a single optical fiber coupled to receive a modulated output signal from the active integrated optical interferometer; and
a beam splitter coupled to the single optical fiber that splits the modulated signal into two light beam parts including a signal beam that is sent to a sample and then reflected to the photodetector, and a reference beam that is sent directly to the photodetector.

22. The sensor according to claim 14 wherein the optical modulator and interferometer further comprise:
an active integrated optical interferometer cascaded with a two-beam interference formed by a plurality of collimating lenses, the two-beam interference further comprising:
a fiber coupler coupled to receive and split a modulated output signal from the active integrated optical interferometer, a first collimating lens being directed into a sample and a second collimating lens being directed to the photodetector, reflected light from the sample forming a signal beam that interferes with a reference beam of collimated light from the second collimating lens at the photodetector.

23. The sensor according to claim 14 wherein the optical modulator and interferometer further comprise:
two cascaded interferometers including an active integrated optical interferometer followed by a second interferometer having a waveguide light splitter, a collimating lens, a focusing lens, and a reference mirror,
the reference mirror and a sample being configured to reflect light to the photodetector.

24. The sensor according to claim 14 wherein:
the photodetector is a single element for one-dimensional, single-point detection.

25. The sensor according to claim 14 wherein: the photodetector is a two-dimensional array of elements for two-dimensional detection.

26. The sensor according to claim 14 wherein the optical modulator end interferometer further comprise:
an active integrated optical interferometer; and
a double fiber array cascaded with the active integrated optical interferometer and including a fiber collimating lens, a focusing lens, an electrical band-pass filter, a source head, and a detector head.

27. The sensor according to claim 14 wherein the optical modulator and interferometer further comprise:
an amplitude modulator; and
a fiber coupler cascaded with the amplitude modulator and including a fiber collimating lens, a focusing lens, an electrical band-pass filter, a source head, and a detector head.

28. The sensor according to claim 27 wherein the amplitude modulator is a Mach-Zender modulator or an electro-absorptive modulator.

29. The sensor according to claim 14 wherein the optical modulator and interferometer further comprise:
an amplitude modulator; and
a bulk optic or fiber-optic Michelson interferometer in a configuration to form a probe beam normal to a sample and using focusing optics to focus a pump beam on the sample.

30. The sensor according to claim 14 further comprising:
a pulsed laser coupled to evoke an acoustic signal through the interferometer.

31. The sensor according to claim 30 further comprising:
a microscope objective lens coupled to focus light generated by the pulsed laser.

32. The sensor according to claim 14 wherein:
the optical modulator is selected from a group consisting of a Mach-Zender modulator, an electro-absorption modulator, a polarization modulator, internal modulation of a direct-modulated laser, and an electro-optic modulator configured as a straight channel waveguide or bulk crystal with input and output polarizers.

33. The sensor according to claim 14 wherein:
the photodetector combines the acoustic signal and the modulation signal;
at a zero bias point the interferometer has a quadratic response; and
phase modulation on light caused by a vibrating surface of a sample or caused by an elastic wave-induced change in refractive index near a surface of the sample mixes with phase modulation generated by the optical modulator.

34. The sensor according to claim 14 wherein:
the acoustic signal is in a gigahertz range and is down-converted to a kilohertz to megahertz range for detection by the photodetector which detects signals in the kilohertz to megahertz range.

35. A method of acquiring subsurface structural information comprising:
illuminating a sample under test with pulsed laser signals that propagate shock waves through the sample;

detecting reflected light entering a top layer of the sample and reflecting from underlying subsurface structure, the reflected light being phase modulated due to changes in refractive index;

mixing the phase modulation with a modulating signal whereby the phase modulated signal is down-converted to a lower frequency signal;

measuring a surface vibration signature of a micro or nano structure of the sample induced by comparison of acoustic responses of the pulsed laser signal; and indicating information relating to subsurface structure based on the surface vibration signature.

36. The method according to claim 35 further comprising:
analyzing surface vibration acoustical spectra of the sample for resonance frequency and amplitude information indicative of size and severity of defects in a single layer or a final layer of a multiple-layer structure.

37. The method according to claim 35 further comprising:
analyzing acoustic resonance in a high frequency range.

38. The method according to claim 37 further comprising:
down-converting the high frequency range acoustic resonance signals to lower frequencies for usage by lower noise and higher gain detectors.

39. The method according to claim 35 further comprising:
indicating information relating to subsurface structure based on the surface vibration signature selected from a group of information consisting of delamination of a layer, internal cracks, thickness variation, damaged microstructures, presence of microstructures, damaged surface, and subsurface structures.

40. A method of acquiring subsurface structural information comprising:
illuminating a multiple-layer sample under test with a pulsed laser signal that excites elastic waves propagating normal to a sample surface, reflecting from multiple-layer surfaces back to the surface;

detecting reflected light entering a top layer of the sample and reflecting from underlying subsurface structure, the reflected light being phase modulated due to changes in refractive index;

mixing the phase modulation with a modulating signal whereby the phase modulated signal is down-converted to a lower frequency signal;

measuring changes in refractive index near a surface of the sample under test induced by the pulsed laser signal by analyzing acoustic resonance; and indicating information relating to subsurface structure based on the changes in refractive index.

41. The method according to claim 40 further comprising:
analyzing acoustic resonance in a high frequency range.

42. The method according to claim 41 further comprising:
down-converting the high frequency range acoustic resonance signals to lower frequencies for usage by lower noise and higher gain detectors.

43. The method according to claim 40 further comprising:
calibrating instruments used in acquiring subsurface structural information comprising:
supplying multiple-layer sample parameters;
scanning an acoustic resonance spectrum;
observing a peak spectral element at a lower frequency end of the spectrum;
determining a vibration amplitude based on a test modulation amplitude; and
determining relative phase difference between resonances based on spectrum shape.

44. The method according to claim 40 further comprising:
modulating optical properties including refractive index and absorption induced by illuminating the multiple-layer sample that activates an elastic wave and generates strain in the sample, reflected light from the illumination being phase-modulated by the modulated refractive index;

mixing the phase-modulated reflected light with an electro-optic modulation signal; and down-converting the mixed signal to a lower frequency signal.

45. The method according to claim 40 further comprising:
analyzing non-linear elastic responses of the sample in terms of harmonic acoustic resonance, and sum and difference acoustic frequencies; and
assessing damage according to the analysis.

46. The method according to claim 40 further comprising:
focusing a pulsed laser beam in a line using a cylindrical lens;
rotating the sample with respect to a sensor or pulse laser to modulate acoustic response in presence of anisotropy; and
assessing anisotropy.

47. The method according to claim 40 further comprising:
indicating information relating to subsurface structure based on the surface vibration signature selected from a group of information consisting of delamination of a layer, internal cracks, thickness variation, damaged microstructures, presence of microstructures, damaged surface, and subsurface structures.

* * * * *